US009545334B2

United States Patent
Steen et al.

(10) Patent No.: US 9,545,334 B2
(45) Date of Patent: Jan. 17, 2017

(54) SYSTEM AND METHOD FOR MODULATED SURGICAL PROCEDURE IRRIGATION AND ASPIRATION

(75) Inventors: Mark E. Steen, Chino Hills, CA (US); Kenneth E. Kadziauskas, Coto de Caza, CA (US)

(73) Assignee: Abbott Medical Optics, Inc., Santa Ana, CA (US)

(*) Notice: Subject to any disclaimer, the term of this patent is extended or adjusted under 35 U.S.C. 154(b) by 207 days.

(21) Appl. No.: 12/927,631

(22) Filed: Nov. 18, 2010

(65) Prior Publication Data

US 2011/0071460 A1    Mar. 24, 2011

Related U.S. Application Data

(62) Division of application No. 10/619,088, filed on Jul. 14, 2003, now Pat. No. 7,846,126.

(51) Int. Cl.
    A61B 17/20     (2006.01)
    A61F 9/00      (2006.01)
    A61F 9/007     (2006.01)
    A61M 1/00      (2006.01)

(52) U.S. Cl.
    CPC ....... *A61F 9/00745* (2013.01); *A61F 9/00736* (2013.01); *A61M 1/0037* (2013.01)

(58) Field of Classification Search
    CPC ... A61M 1/0037; A61F 9/007; A61F 9/00736; A61F 9/00745
    USPC ...... 604/22, 27, 28, 32, 35, 289, 294; 606/4, 606/107
    See application file for complete search history.

(56) References Cited

U.S. PATENT DOCUMENTS

| | | |
|---|---|---|
| 2,434,480 A | 1/1948 | Anderson |
| 3,941,122 A | 3/1976 | Jones |
| 4,184,510 A | 1/1980 | Murry et al. |
| 4,274,411 A | 6/1981 | Dotson, Jr. |
| 4,324,243 A | 4/1982 | Helfgott et al. |
| 4,702,733 A | 10/1987 | Wright et al. |
| 4,808,948 A | 2/1989 | Patel et al. |
| 4,827,911 A | 5/1989 | Broadwin et al. |
| 4,954,960 A | 9/1990 | Lo et al. |
| 4,970,656 A | 11/1990 | Lo et al. |
| 4,983,901 A | 1/1991 | Lehmer |
| 5,001,649 A | 3/1991 | Lo et al. |
| 5,209,221 A | 5/1993 | Riedlinger |
| 5,279,547 A | 1/1994 | Costin |
| 5,318,563 A | 6/1994 | Malis et al. |
| 5,331,951 A | 7/1994 | Kepley |

(Continued)

FOREIGN PATENT DOCUMENTS

| | | |
|---|---|---|
| DE | 19940712 | 8/1999 |
| DE | 19940712 A1 | 3/2001 |

(Continued)

*Primary Examiner* — Nathan R Price
(74) *Attorney, Agent, or Firm* — Smyrski Law Group, A P.C.

(57) ABSTRACT

A method and apparatus for performing modulated fluid delivery and aspiration during a surgical procedure such as phacoemulsification is provided. The method and apparatus include delivering fluid and/or aspirating fluid in a modulated or pulsed manner during a surgical procedure, including applying fluid and/or aspirating fluid in connection with ultrasonic energy at a level and for a time period sufficient to induce transient cavitation. Fluid may be applied and/or aspirated at a timing sequence and duty cycle similar to or different from application of ultrasonic energy delivery.

34 Claims, 22 Drawing Sheets

(56) References Cited

U.S. PATENT DOCUMENTS

| | | |
|---|---|---|
| 5,370,602 A | 12/1994 | Kepley |
| 5,388,569 A | 2/1995 | Kepley |
| 5,406,503 A | 4/1995 | Williams, Jr. et al. |
| 5,431,664 A | 7/1995 | Ureche et al. |
| 5,453,087 A | 9/1995 | Malinowski |
| 5,520,633 A | 5/1996 | Costin |
| 5,547,459 A | 8/1996 | Kaufman et al. |
| 5,582,578 A | 12/1996 | Zhong et al. |
| 5,591,127 A | 1/1997 | Barwick, Jr. et al. |
| 5,674,226 A | 10/1997 | Doherty et al. |
| 5,700,240 A | 12/1997 | Barwick, Jr. et al. |
| 5,733,256 A | 3/1998 | Costin |
| 5,800,365 A | 9/1998 | Zhong et al. |
| 5,808,396 A | 9/1998 | Boukhny |
| 5,852,794 A | 12/1998 | Staggs |
| 5,979,494 A | 11/1999 | Perkins et al. |
| 6,161,545 A | 12/2000 | Chow |
| 6,203,516 B1 | 3/2001 | Kepley |
| 6,319,220 B1 | 11/2001 | Bylsma |
| 6,322,533 B1 | 11/2001 | Gonon |
| 6,391,042 B1 | 5/2002 | Cimino |
| 6,423,028 B1 | 7/2002 | Gonon |
| 6,589,204 B1 | 7/2003 | Sussman et al. |
| 6,699,212 B1 | 3/2004 | Kadziauskas et al. |
| 7,846,126 B2 | 12/2010 | Steen et al. |
| 2002/0082793 A1 | 6/2002 | Kadziauskas et al. |

FOREIGN PATENT DOCUMENTS

| | | |
|---|---|---|
| EP | 0270819 | 6/1988 |
| EP | 270819 A2 | 6/1988 |
| EP | 336620 A2 | 10/1989 |
| EP | 0336620 | 12/1993 |
| EP | 336620 B1 | 12/1993 |
| JP | 06189972 | 7/1994 |
| JP | 6189972 A2 | 7/1994 |
| JP | 2001161740 | 6/2001 |
| JP | 2001161740 A2 | 6/2001 |
| WO | WO 95/20374 | 8/1995 |
| WO | WO9520374 A1 | 8/1995 |
| WO | WO 00/51508 | 9/2000 |
| WO | WO0051508 A1 | 9/2000 |
| WO | WO 00/64388 | 11/2000 |
| WO | WO0064388 A1 | 11/2000 |
| WO | WO 01/13838 | 3/2001 |
| WO | WO0113838 A1 | 3/2001 |

SYSTEM AND METHOD FOR MODULATED SURGICAL PROCEDURE IRRIGATION AND ASPIRATION

This application is a divisional of co-pending U.S. patent application Ser. No. 10/619,088, entitled "System and Method for Modulated Surgical Procedure Irrigation and Aspiration," inventors Mark E. Steen et al., filed Jul. 14, 2003, the entirety of which is hereby incorporated by reference.

BACKGROUND OF THE INVENTION

Field of the Invention

The present invention relates generally to the field of surgical tissue removal systems, and more specifically to modulated irrigation and aspiration during surgical procedures such as phacoemulsification.

Description of the Related Art

Phacoemulsification surgery has been successfully employed in the treatment of certain ocular problems, such as cataracts. Phacoemulsification surgery utilizes a small corneal incision to insert the tip of at least one phacoemulsification handheld surgical implement, or handpiece. The handpiece includes a needle which is ultrasonically driven once placed within an incision to emulsify the eye lens, or break the cataract into small pieces. The broken cataract pieces may subsequently be removed using the same handpiece or another handpiece in a controlled manner. The surgeon may then insert lens implants in the eye through the incision. The incision is allowed to heal, and the results for the patient are typically significantly improved eyesight.

As may be appreciated, the flow of fluid to and from a patient through a fluid infusion or extraction system and power control of the phacoemulsification handpiece is critical to the procedure performed. Different medically recognized techniques have been utilized for the lens removal portion of the surgery. Among these, one popular technique is a simultaneous combination of phacoemulsification, irrigation and aspiration using a single handpiece. This method includes making the incision, inserting the handheld surgical implement to emulsify the cataract or eye lens. Simultaneously with this emulsification, the handpiece provides a fluid for irrigation of the emulsified lens and a vacuum for aspiration of the emulsified lens and inserted fluids.

Currently available phacoemulsification systems include a variable speed peristaltic pump, a vacuum sensor, an adjustable source of ultrasonic power, and a programmable microprocessor with operator-selected presets for controlling aspiration rate, vacuum and ultrasonic power levels. A phacoemulsification handpiece is interconnected with a control console by an electric cable for powering and controlling the piezoelectric transducer. Tubing provides irrigation fluid to the eye and enables withdrawal of aspiration fluid from an eye through the handpiece. The hollow needle of the handpiece may typically be driven or excited along its longitudinal axis by the piezoelectric effect in crystals created by an AC voltage applied thereto. The motion of the driven crystal is amplified by a mechanically resonant system within the handpiece such that the motion of the needle connected thereto is directly dependent upon the frequency at which the crystal is driven, with a maximum motion occurring at a resonant frequency. The resonant frequency is dependent in part upon the mass of the needle interconnected therewith, which is typically vibrated by the crystal.

Power control of the phacoemulsification handpiece is highly critical to successful phacoemulsification surgery. Certain previous systems address the requirements of power control for a phacoemulsification handpiece based on the phase angle between voltage applied to a handpiece piezoelectric transducer and the current drawn by the piezoelectric transducer and/or the amplitude of power pulses provided to the handpiece. The typical arrangement is tuned for the particular handpiece, and power is applied in a continuous fashion or series of solid bursts subject to the control of the surgeon/operator. For example, the system may apply power for 150 ms, then cease power for 350 ms, and repeat this on/off sequence for the necessary duration of power application. In this example, power is applied through the piezoelectric crystals of the phacoemulsification handpiece to the needle causing ultrasonic power emission for 150 ms, followed by ceasing application of power using the crystals, handpiece, and needle for 350 ms. It is understood that while power in this example is applied for 150 ms, this application of power includes application of a sinusoidal waveform to the piezoelectric crystals at a frequency of generally between about 25 kHz and 50 kHz and is thus not truly "constant." Application of power during this 150 ms period is defined as a constant application of a 25 kHz to 50 kHz sinusoid. In certain circumstances, the surgeon/operator may wish to apply these power bursts for a duration of time, cease application of power, then reapply at this or another power setting. The frequency and duration of the burst is typically controllable, as is the length of the stream of bursts applied to the affected area. The time period where power is not applied enable cavitation in the affected area whereby broken sections may be removed using aspiration provided by the handpiece or an aspiration apparatus.

As described in U.S. patent application Ser. No. 10/387, 327 to Kadziauskas et al., entitled "System and Method for Pulsed Ultrasonic Power Delivery Employing Cavitation Aspects," filed Mar. 12, 2003, discusses the beneficial aspects of transient cavitation and provides a system and method for applying energy at a level and for a time period sufficient to induce transient cavitation, and reducing applied energy after applying energy during a second non-zero lower energy period. Various ultrasonic power delivery profiles may be employed utilizing the beneficial effects of transient cavitation, including more powerful removal with reduced risk of burning or damaging the affected area.

Generally, irrigation and aspiration are employed by the surgeon using the device to remove unwanted tissue and maintain pressure within the eye. In the presence of high frequency power applications, cavitation may be generated through the needle to the unwanted tissue in an effort to break the tissue. Alternately, mechanical fragmentation may be employed using rotary, oscillatory, or reciprocating cutters to segment or grind unwanted tissue. The resultant tissue is aspirated in slurry form from the surgical site.

Issues associated with aspiration and irrigation in this environment can include difficulty in acquiring or purchasing the tissue and holding the tissue with the tip for proper removal. Use of pulsed ultrasonic power delivery, and capture and removal of unwanted tissue, particularly in high power environments where transient cavitation is encountered, can be difficult. Power delivery in the presence of relatively constant or slowly changing fluid flow characteristics can cause disruption of purchase, holding, and removal of unwanted tissue. Additionally, a mechanical cavity or cavitation cloud may form in the presence of ultrasonic cavitational energy, and such a mechanical cavity can provide a virtual barrier to efficient tissue processing. Such a mechanical cavity results from pressure differentials formed by ultrasonic energy application in the presence of a relatively constant fluid flow, and is undesirable.

Further, in the environment described, tissue may occasionally clog the lumen, or fluid passage, within the tip of the handpiece. Such clogging creates unpredictable performance characteristics and can result in undesirable pressure surges. The vacuum levels typically employed with aspiration and irrigation tend to be low to avoid clogging and other undesirable fluid flow effects. Use of low pressure can inhibit a surgeon's ability to purchase and hold unwanted tissue.

Based on the foregoing, it would be advantageous to provide an irrigation and aspiration system that effectively and efficiently operates in the presence of high ultrasonic power delivery, such as systems generating transient cavitation, and minimizes those drawbacks associated with previous tissue removal systems.

SUMMARY OF THE INVENTION

According to a first aspect of the current design, there is provided an apparatus comprising a handpiece having a needle and electrical means for ultrasonically vibrating said needle, power source means for providing pulsed electrical power to the handpiece electrical means, input means for enabling an operator to select an amplitude of the electrical pulses, irrigation means for providing fluid during a surgical procedure conducted in a surgical environment, said irrigation means providing fluid during at least one modulated fluid burst period, said modulated fluid burst period comprising a fluid pulse within the surgical environment, followed by a de minimis fluid pulse, and control means for controlling power supplied to the handpiece.

According to a second aspect of the current design, there is provided an apparatus comprising a handpiece having a needle and electrical means for ultrasonically vibrating said needle, power source means for providing pulsed electrical power to the handpiece electrical means, input means for enabling an operator to select an amplitude of the electrical pulses, irrigation means for providing fluid from the handpiece, said fluid providing means controlling fluid provided by applying fluid for a fluid pulse period followed by applying de minimis fluid during a fluid pause period, and control means for controlling power supplied to the handpiece.

According to a third aspect of the current design, there is provided a method for delivering fluid to an ocular region during a phacoemulsification procedure. The method comprises irrigating the ocular region by applying a series of modulated fluid pulses to the ocular region via a fluid control device.

According to a fourth aspect of the current design, there is provided a method of delivering fluid to a region during a tissue removal procedure, comprising delivering modulated fluid pulses during an on period, fluid pulse delivery comprising delivering at least one pulse of fluid having a relatively high amplitude, and delivering a de minimis quantity of fluid after delivering every high amplitude fluid pulse.

According to a fifth aspect of the current design, there is provided a surgical apparatus. The surgical apparatus comprises means for applying fluid to an area. The applying means comprise irrigation means for applying modulated fluid pulses during a plurality of short burst periods, said short burst periods comprising a fluid burst period followed a predetermined time thereafter by a de minimis fluid delivery period.

According to a sixth aspect of the current design, there is provided a method for providing modulated fluid pulses to an ocular region during a phacoemulsification procedure. The method comprises applying fluid to the ocular region using at least one modulated fluid pulse period. Each modulated fluid pulse period comprises applying fluid to the ocular region using a fluid pulse for a first period of time, and applying de minimis fluid to the ocular region for a second period of time.

According to a seventh aspect of the current design, there is provided a method for providing fluid during a surgical procedure. The method comprises providing fluid using a fluid control device during a plurality of pulse periods, said pulse periods comprising a fluid surge period followed by a fluid pause period, wherein fluid applied during the fluid surge period is greater than fluid applied during the fluid pause period.

According to an eighth aspect of the current design, there is provided an apparatus comprising a handpiece having a needle and electrical means for ultrasonically vibrating the needle, power source means for providing pulsed electrical power to the handpiece electrical means, input means for enabling an operator to select an amplitude of the electrical pulses, aspiration means for aspirating fluid during a surgical procedure conducted in a surgical environment, the aspiration means receiving fluid during at least one modulated fluid burst period, the modulated fluid burst period comprising a negative pressure differential pulse delivered to the surgical environment, followed by a de minimis pressure differential pulse transmission; and control means for controlling power supplied to the handpiece.

According to a ninth aspect of the current design, there is provided a method for aspirating fluid from an ocular region during a phacoemulsification procedure. The method comprises aspirating the ocular region by applying a series of modulated differential pressure pulses to the ocular region via a fluid control device.

These and other objects and advantages of all aspects of the present design will become apparent to those skilled in the art after having read the following detailed disclosure of the preferred embodiments illustrated in the following drawings.

DESCRIPTION OF THE DRAWINGS

The present invention is illustrated by way of example, and not by way of limitation, in the figures of the accompanying drawings in which.

DETAILED DESCRIPTION OF THE INVENTION

Device.

Figure 1:
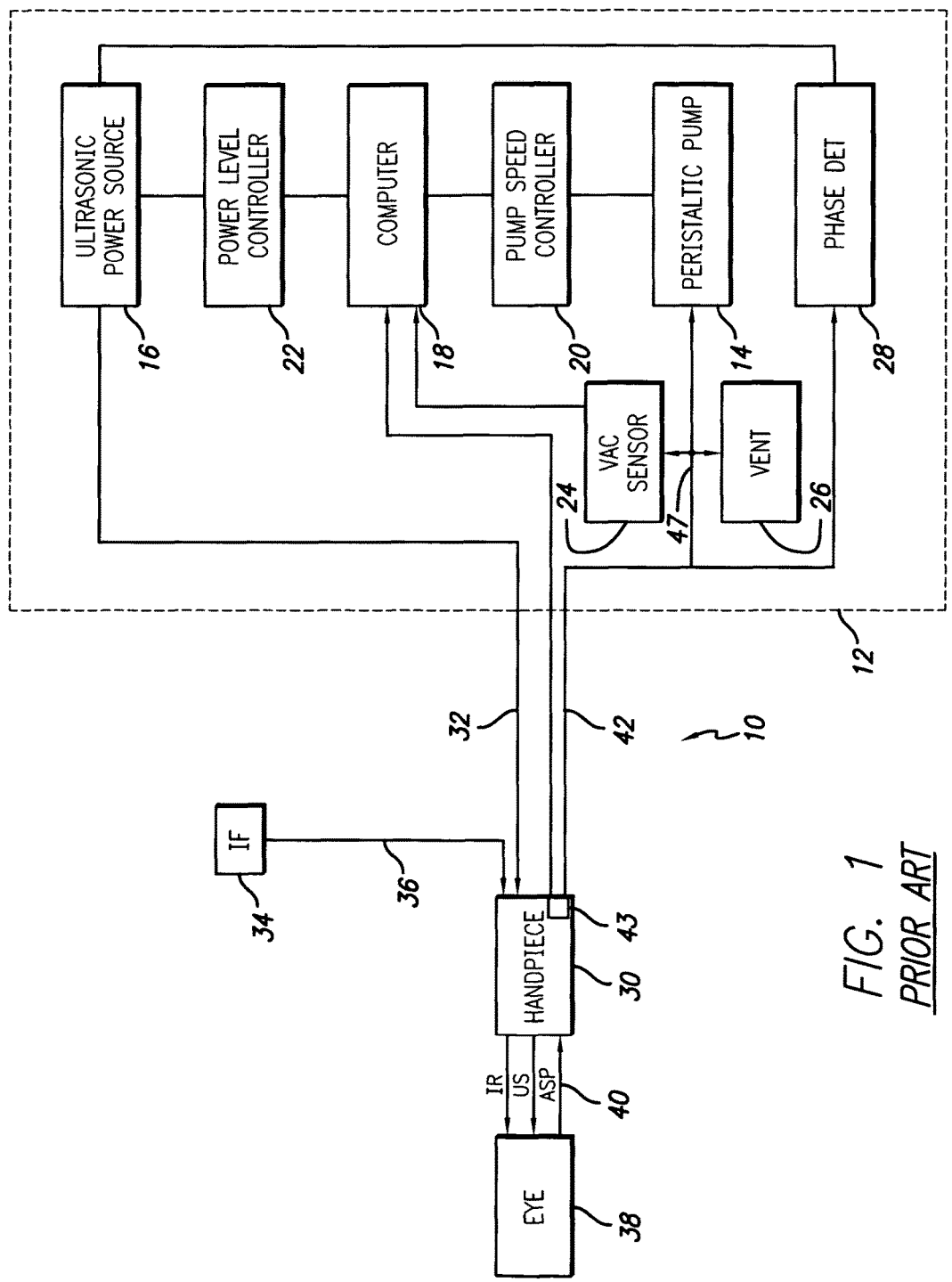
FIG. 1 is a functional block diagram of a prior art phacoemulsification system.

FIG. 1 illustrates a phacoemulsification system in block diagram form, indicated generally by the reference numeral 10. The system has a control unit 12, indicated by the dashed lines in FIG. 1 which includes a variable speed peristaltic pump 14, which provides a vacuum source, a source of pulsed ultrasonic power 16, and a microprocessor computer 18 that provides control outputs to pump speed controller 20 and ultrasonic power level controller 22. A vacuum sensor 24 provides an input to computer 18 representing the vacuum level on the input side of peristaltic pump 14. Suitable venting is provided by vent 26.

A phase detector 28 provides an input to computer 18 representing a phase shift between a sine wave representation of the voltage applied to a handpiece/needle 30 and the resultant current into the handpiece 30. The block representation of the handpiece 30 includes a needle and electrical means, typically a piezoelectric crystal, for ultrasonically vibrating the needle. The control unit 12 supplies power on line 32 to a phacoemulsification handpiece/needle 30. An irrigation fluid source 34 is fluidly coupled to handpiece/needle 30 through line 36. The irrigation fluid and ultrasonic power are applied by handpiece/needle 30 to a patient's eye, or affected area or region, indicated diagrammatically by block 38, and may include a lumen (not shown). Alternatively, the irrigation source may be routed to the eye 38 through a separate pathway independent of the handpiece. The eye 38 is aspirated by the control unit peristaltic pump 14 through line/handpiece needle 40 and line 42. A switch 43 disposed on the handpiece 30 may be utilized as a means for enabling a surgeon/operator to select an amplitude of electrical pulses to the handpiece via the computer 18, power level controller 22 and ultrasonic power source 16 as discussed herein. Any suitable input means, such as, for example, a foot pedal (not shown) may be utilized in lieu of the switch 43.

Figure 2:
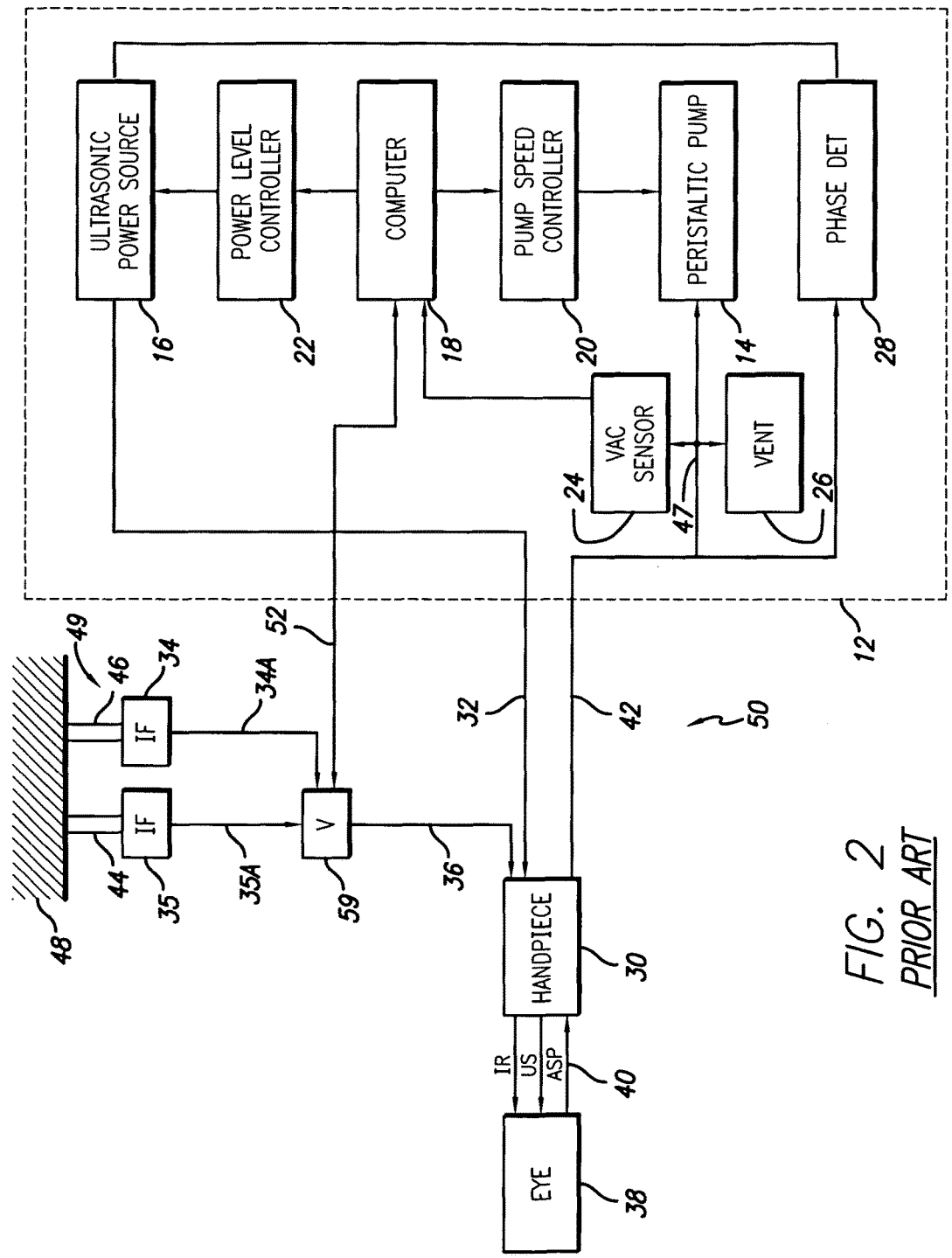
FIG. 2 is a functional block diagram of an alternative aspect of a prior art phacoemulsification system including apparatus for providing irrigation fluid at more than one pressure to a handpiece.

FIG. 2 shows an alternative phacoemulsification system 50 incorporating all of the elements of the system 10 shown in FIG. 1, with identical reference characters identifying components, as shown in FIG. 1. In addition to the irrigation fluid source 34, a second irrigation fluid source 35 is provided with the sources 34, 35 being connected to the line 36 entering the handpiece/needle 30 through lines 34a, 35a, respectively, and to a valve 59. The valve 59 functions to alternatively connect line 34A and source 34 and line 35A and source 35 with the handpiece/needle 30 in response to a signal from the power level controller 22 through a line 52.

As shown, irrigation fluid sources 34, 35 are disposed at different heights above the handpiece/needle 30 providing a means for introducing irrigation fluid to the handpiece at a plurality of pressures, the head of the fluid in the container 35 being greater than the head of fluid in the container 34. A harness 49, including lines of different lengths 44, 46, when connected to the support 48, provides a means for disposing the containers 34, 35 at different heights over the handpiece/needle 30.

The use of containers for irrigation fluids at the various heights is representative of the means for providing irrigation fluids at different pressures, and alternatively, separate pumps may be provided with, for example, separate circulation loops (not shown). Such containers and pumps can provide irrigation fluid at discrete pressures to the handpiece/needle 30 upon a command from the power controller 22.

Operation.

Figure 3A:
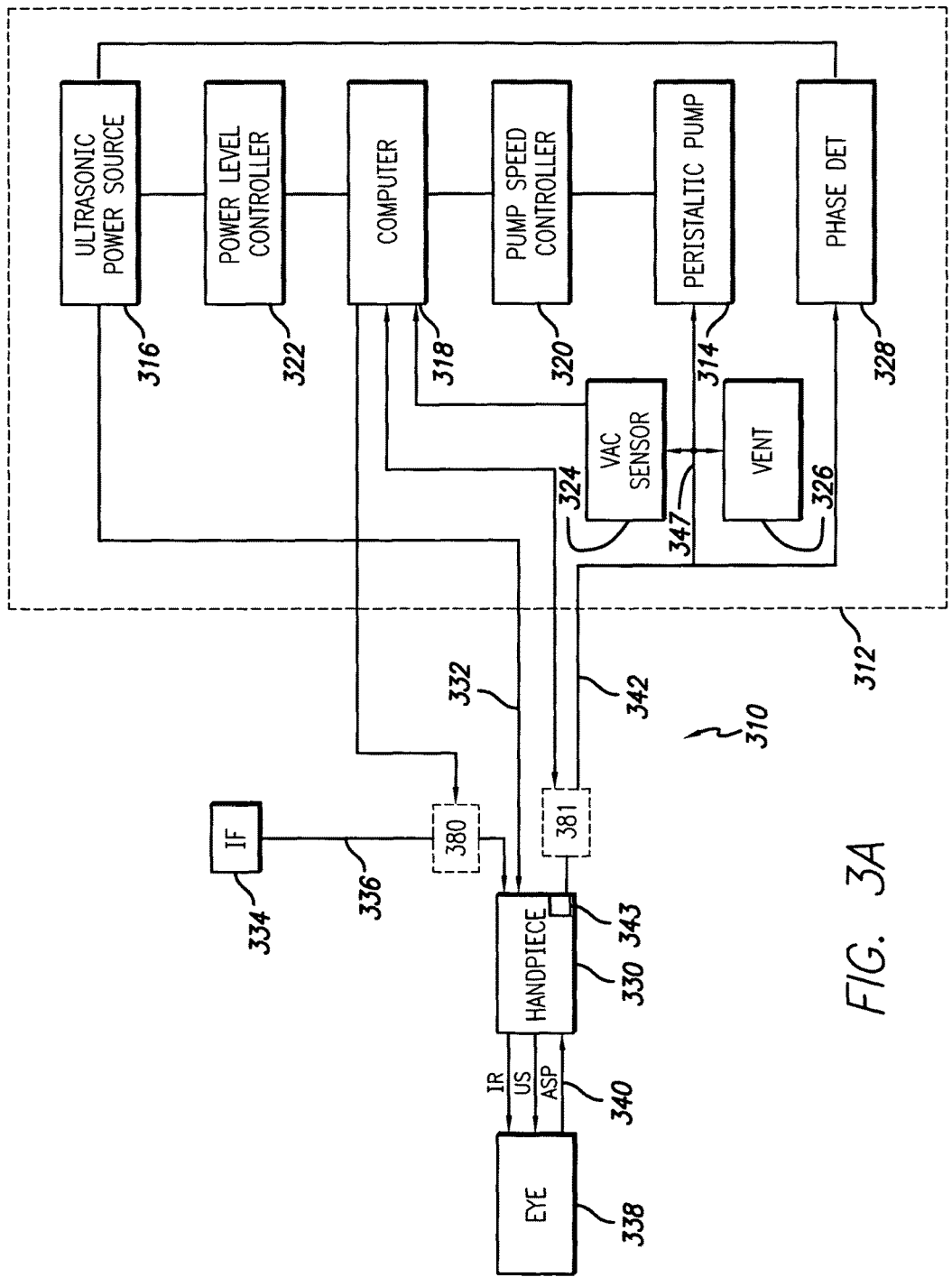
FIG. 3A is a functional block diagram of a phacoemulsification system having the ability to provide modulated irrigation and/or aspiration in accordance with one aspect of the present invention.

The present design, shown in FIG. 3A, generates a pulse assisted waveform either in phase or out of phase with the ultrasonic power source 316 as monitored and provided by computer 318. The pulsed irrigation uses irrigation fluid generated by irrigation fluid source 334 in a pulsing manner, timed to propagate the length of the tubing 336 between the irrigation fluid source 334 and handpiece 330 and arrive at the tip-tissue interface either randomly or in sequence or collaboration with the modulated ultrasonic action.

From FIG. 3A, system 300 includes a control unit 312 having a variable speed peristaltic pump 314, which provides a vacuum source, a source of pulsed ultrasonic power 316, and a microprocessor computer 318 that provides control outputs to pump speed controller 320, ultrasonic power level controller 322, and irrigation control unit 380. Vacuum sensor 324 provides an input to computer 318 representing the vacuum level on the input side of peristaltic pump 314. Suitable venting is provided by vent 326.

Phase detector 328 provides an input to computer 318 representing a phase shift between a sine wave representation of the voltage applied to a handpiece/needle 330 and the resultant current into the handpiece 330. The block representation of the handpiece 330 again includes a needle and electrical means for ultrasonically vibrating the needle. The control unit 312 supplies power on line 332 to a phacoemulsification handpiece/needle 330. An irrigation fluid source 334 is fluidly coupled to handpiece/needle 330 through line 336. The irrigation fluid and ultrasonic power are applied by handpiece/needle 330 to a patient's eye, or affected area or region, indicated diagrammatically by block 338. Alternatively, the irrigation source may be routed to the eye 338 through a separate pathway independent of the handpiece. The eye 338 is aspirated by the control unit peristaltic pump 314 through line/handpiece needle 340 and line 342, as controlled by irrigation control unit 380. A switch 343 disposed on the handpiece 330 may enable the surgeon/operator to select an amplitude of electrical pulses and corresponding irrigation/aspiration pulses to the handpiece 330 via the computer 318, power level controller 322 and ultrasonic power source 316. Again, any suitable input means, such as, for example, a foot pedal (not shown) may be utilized in lieu of the switch 343.

Fluid is aspirated from the eye 338 via aspiration line 340 and handpiece 330. Aspirated fluid may pass to aspiration control unit 381, and from aspiration control unit 381 to peristaltic pump 314, phase detector 328, vent 326, and vacuum sensor 347. Aspiration control unit 381 is controlled by computer 318. Aspiration control unit 381 can provide a series of pressure differential pulses, the pressure differential being between ambient pressure and a negative pressure, thereby propagating through handpiece 330 and aspiration line 340 and pulling fluid from the eye 338.

Pulsed fluid delivery and/or pressure differential pulses operate in conjunction with ultrasonic power delivery in the following manner. Ultrasonic power delivery may cause transient cavitation, defined as the violent collapse of bubbles in the fluid. The system applies ultrasonic power in brief pulses, with these brief pulses having divided energy levels for the phaco environment presented above. In particular, an initial energy period sufficient to induce transient cavitation in the environment, such as ultrasonic power applied at 30 watts for a brief duration, such as 2 ms, may be employed. The 30 watts represents input to the handpiece. Power may, in certain circumstances, be delivered during a second or subsequent energy delivery period, such as, for example, power delivered at 15 watts for a period of 2 ms. However, a single pulse sufficient to induce transient cavitation, followed by a power off period, may be the ultrasonic power profile delivered to the site. Also, a third or subsequent lower energy delivery period may be employed. The goal of the modulated or stepped power delivery arrangement in this power delivery scenario is to initiate needle stroke above the distance necessary to generate transient cavitation as rapidly as possible. Once the power threshold required to induce transient cavitation has been achieved, power may be reduced for the remainder of the pulse.

Figure 3B:
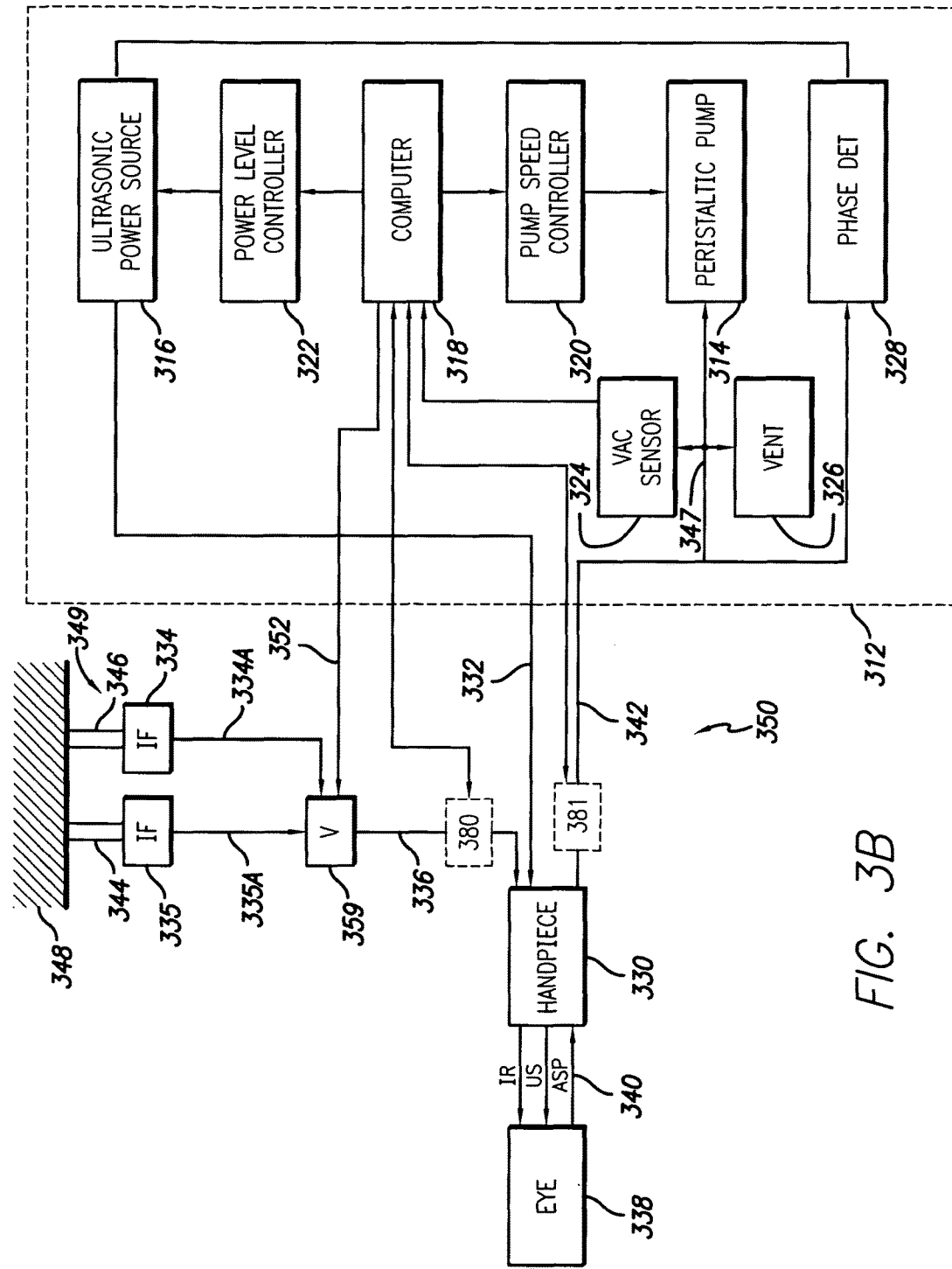
FIG. 3B is a functional block diagram of a phacoemulsification system including apparatus for providing irrigation fluid at more than one pressure to a handpiece and having the ability to provide modulated irrigation and/or aspiration in accordance with another aspect of the present invention.

FIG. 3B shows an alternative phacoemulsification system 350 incorporating all of the elements of the system 310 shown in FIG. 3A, with identical reference characters identifying components. In addition to the irrigation fluid source 334, a second irrigation fluid source 335 is provided with the sources 334, 335 being connected to the line 36 entering the handpiece/needle 330 through lines 334a, 335a, respectively, and to a valve 359. Fluid flowing from valve 359 is controlled by irrigation control unit 380 via computer 318. The valve 359 in combination with irrigation control unit 380 functions to alternatively connect line 334A to source 334 and line 335A to source 335 with the handpiece/needle 330 in response to a signal from the power level controller 322 through line 352.

As shown, irrigation fluid sources 334, 335 are disposed at different heights above the handpiece/needle 330 providing a means for introducing irrigation fluid to the handpiece at varying pressures, the head of the fluid in the container 335 being greater than the head of fluid in the container 334. A harness 349, including lines of different lengths 344, 346, when connected to the support 348, provides a means for disposing the containers 334, 335 at different heights over the handpiece/needle 330. Aspiration may optionally operate in a similar manner to that shown in FIG. 3A.

Fluid is provided in a pulsed manner using the irrigation control unit or control device, which regulates fluid flow, particularly fluid pulse timing. Aspiration is provided in a pulsed manner as well, using the aspiration control unit or control device, which regulates fluid flow by introducing pressure differentials to the aspiration line. While the following description is directed to modulated delivery of pulses in irrigating the area, similar control devices may be employed in aspirating fluid from the region. The control devices used to irrigate may be employed to aspirate in a modulated manner as described above.

While both FIG. 3A and FIG. 3B illustrate modulated irrigation and aspiration elements 380 and 381 in dashed lines to indicate that they are optional elements, it is to be understood that either aspiration and/or irrigation may be employed in accordance with the present invention, but that at least one of the irrigation control unit 380 and aspiration control unit 381 is to be employed. For example, the modulated aspiration described herein may be employed without modulated irrigation and in the absence of irrigation control unit 380. In such an implementation, handpiece 330 would receive fluid either directly from container 334 or valve 359 without the need for connection to computer 318. Similar alterations may be required if modulated irrigation is employed in the absence of modulated aspiration.

Figure 4:
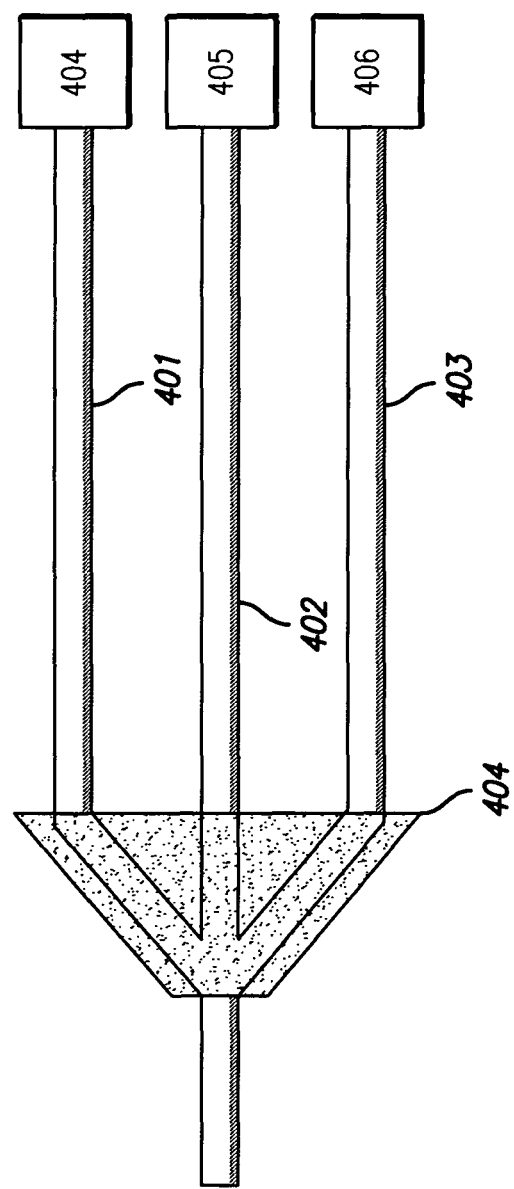
FIG. 4 illustrates a sample aspiration/irrigation control unit.

One aspect of the computer controlled irrigation control unit is presented in FIG. 4. From FIG. 4, the irrigation control unit 380 may have three small flexible tubes 401, 402, and 403 that may be individually molded or formed together and terminate in a manifold 404 to form a parallel flow path. Each of the three flow routes may have a mechanism attached thereto, such as mechanism 404, 405, and/or 406. These mechanisms may be rotary pinch mechanisms or hammer mechanisms as described below, or some other device capable of pulsing fluid at a relatively rapid rate. Each mechanism 404, 405, and 406 has the ability to generate a pulse wave form source, or restrict and permit flow alternately within a relatively short period of time. The pulse wave form propagates the length of tubing 336. The effective frequency of the pressure pulse corresponds to desired action at the tip of the handpiece 330. Pressure waves may be linked in phase with the ultrasonic power delivery or may operate at the harmonic frequency or frequencies of the system or handpiece 330. One timing scheme that may be employed at the aspiration/irrigation control unit 380 is a pulse source set at 120 degrees out of phase, thereby generating a three phase pulse train. Alternately, the irrigation control unit 380 may employ asymmetric pulse modes to enhance traction or disruption at the tip. Further, multiple tube/valve arrangements may be employed to vary the flow to the eye and enhance the aforementioned effects. Such a device may alternately be employed on the aspiration side of the system.

Figure 5A:
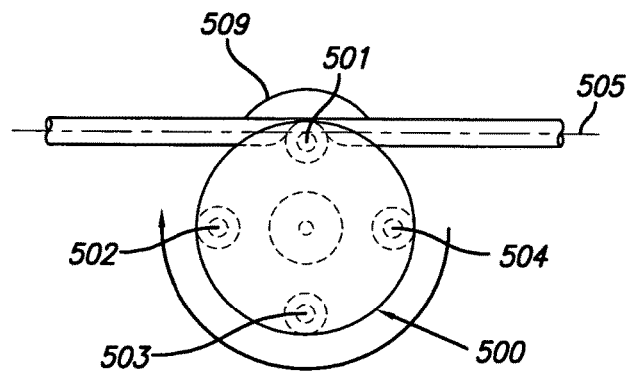
FIG. 5 shows a rotary fluid control device according to one aspect of the present design.
Figure 5B:
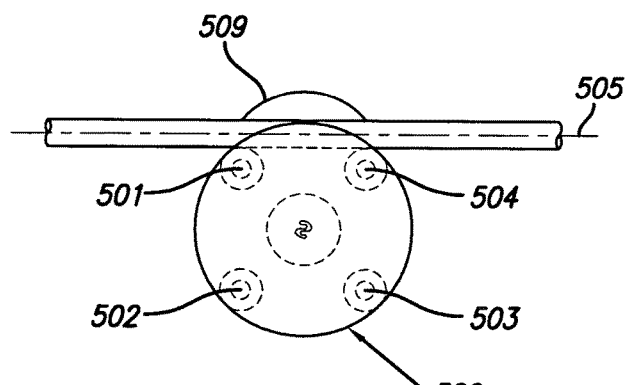
Figure 5C:
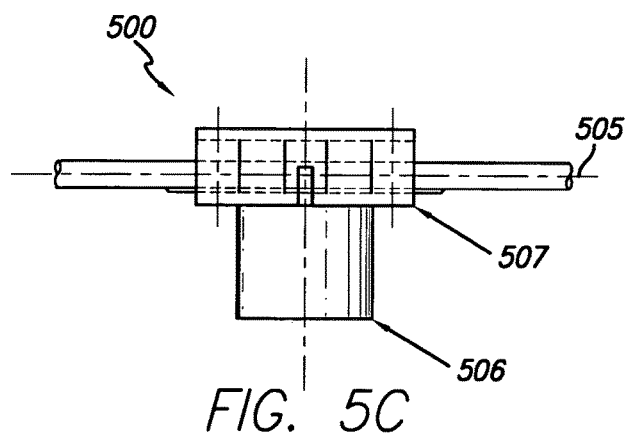

Control of the flow (irrigation or aspiration) through any or all of the small flexible tubes may be performed by various devices. One such device is shown in FIG. 5, which rotates at a rate commanded by the computer. As shown in FIG. 5, four elements 501, 502, 503, and 504 may be employed, but three, five, or more or less pinching elements may be used. FIG. 5A is a top view of a control device 500 with the tube 505 pinched by element 501. FIG. 5B is a top view of the same device 500 unpinched by any element. As with other designs for the control device presented herein, the tube 505 may be constructed from standard material, such as a high strength plastic tubing having sufficient elasticity. The parts of the device 500 such as the element may be constructed of a high strength and high density plastic, or another suitable material, including but not limited to metal. The functionality of the elements is the ability to cause closure or pinching of the tubing in the environment discussed. Note that a support element 509 may be provided to facilitate holding or maintaining of the tubing while pinching occurs. FIG. 5C is a side view of the device 500 having a rotating support member or stepper motor 506 and top element or pump head 507.

Figure 6A:
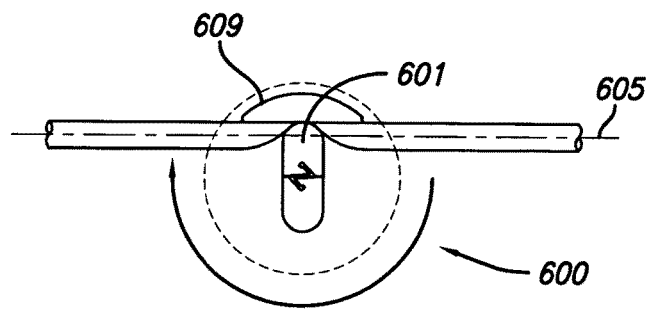
FIG. 6 illustrates another fluid control device according to another aspect of the present design.
Figure 6B:
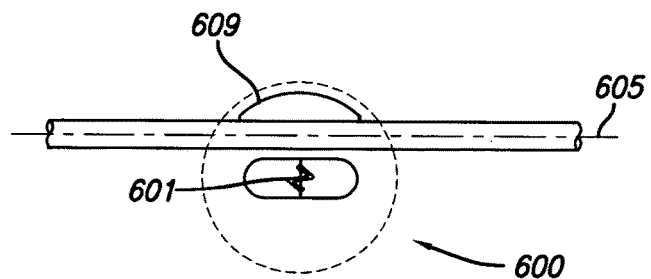
Figure 6C:
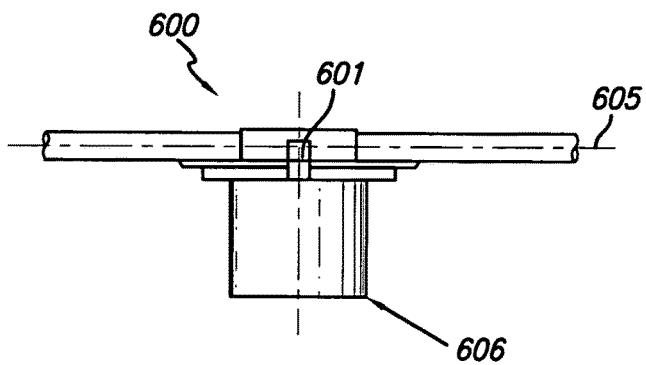
Figure 7A:
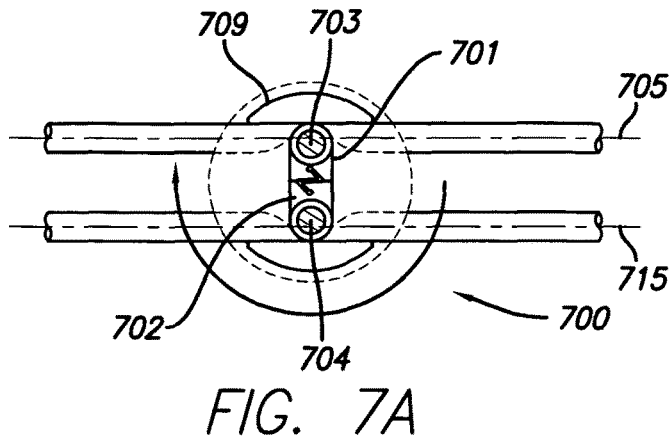
FIG. 7 shows yet another fluid control device according to yet another aspect of the present design.
Figure 7B:
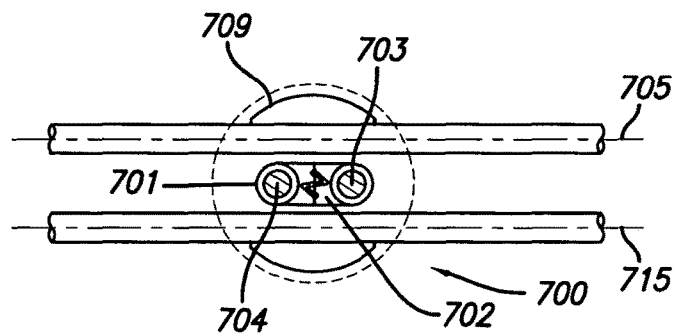
Figure 7C:
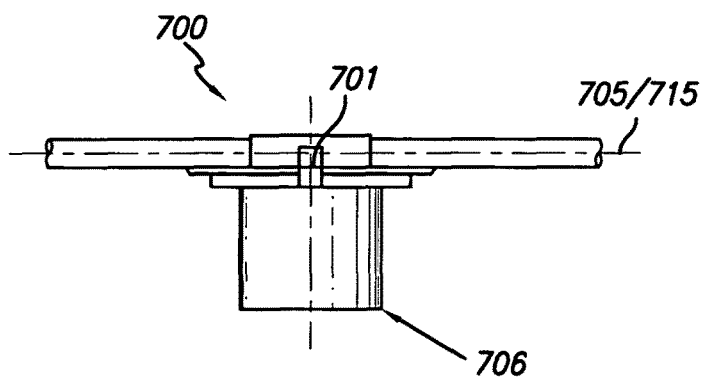

FIG. 6 illustrates an alternate design of a control device 600. FIG. 6A illustrates the rotating pinching by member 601 of tube 605. FIG. 68 shows the member 601 in horizontal position, not pinching the tube 605. FIG. 6C illustrates a side view of the control device 600 with member 601 in a generally parallel orientation to tube 605 similar to the orientation of FIG. 6B. The design of FIG. 6 further illustrates a pump head 607, rotating support member or stepper motor 606, and support element 609. FIG. 7A shows a single rotating member 701 able to restrict flow in two tubes 705 and 715. The rotating member 701 may have a center point 702 as well as two opposing rigid inserts 703 and 704. The rotating member 701 may be formed of plastic, while the rigid inserts 703 and 704 may be cylindrical or near cylindrical metal insert pieces. Other materials may be used that perform the required functionality and are appropriate for the environment. FIG. 7B shows the control device 700 in a non contact orientation. FIG. 7C is a side view of the control device 700 with a single tube 705 in place and shows rotating element 706. A two piece support element 709 is presented here, which may or may not be employed depending on circumstances.

Figure 8A:
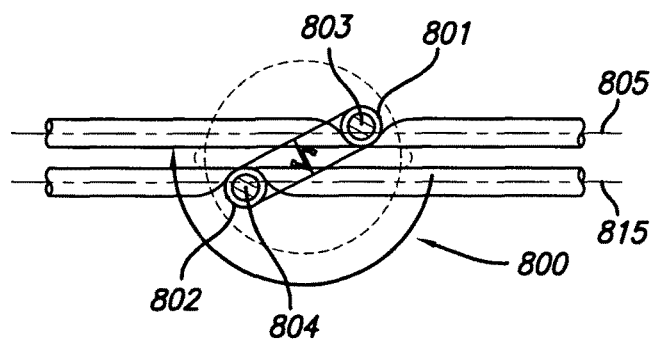
FIG. 8 presents still another fluid control device according to still another aspect of the present design.
Figure 8B:
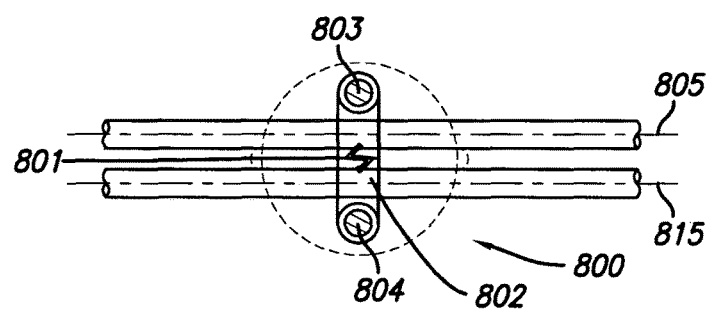
Figure 8C:
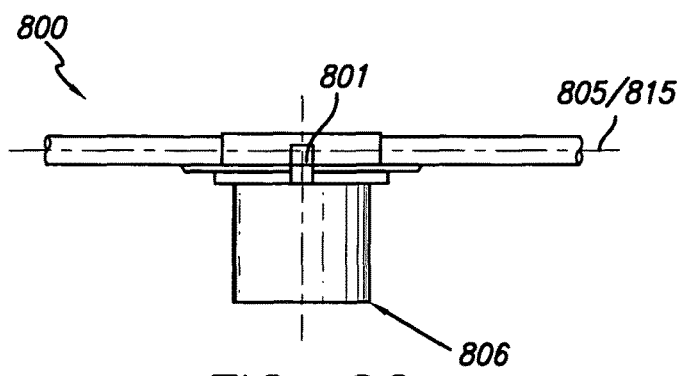
Figure 9A:
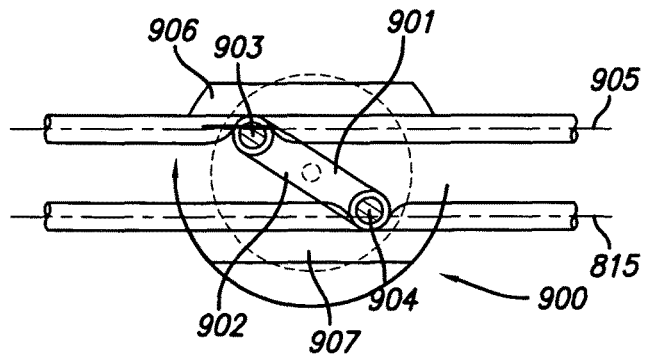
FIG. 9 presents a further fluid control device according to a further aspect of the present design.
Figure 9B:
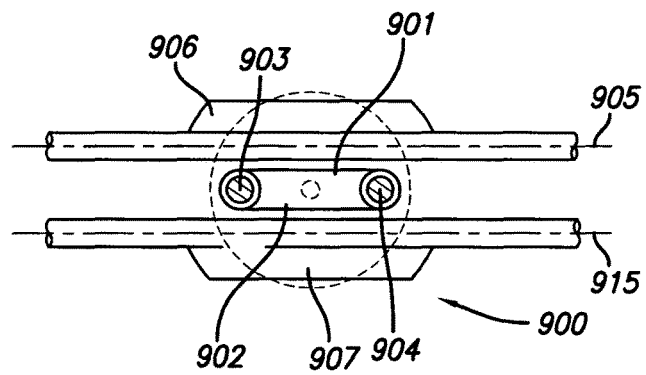
Figure 9C:
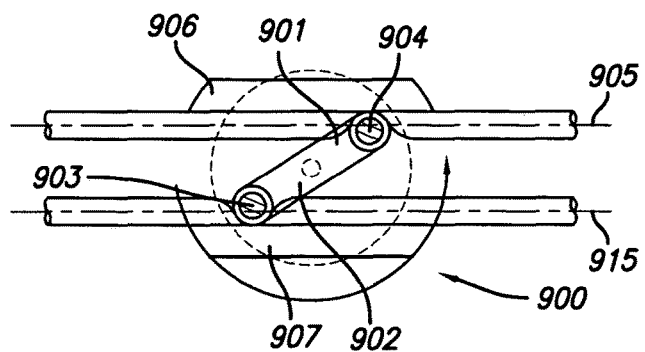
Figure 9D:
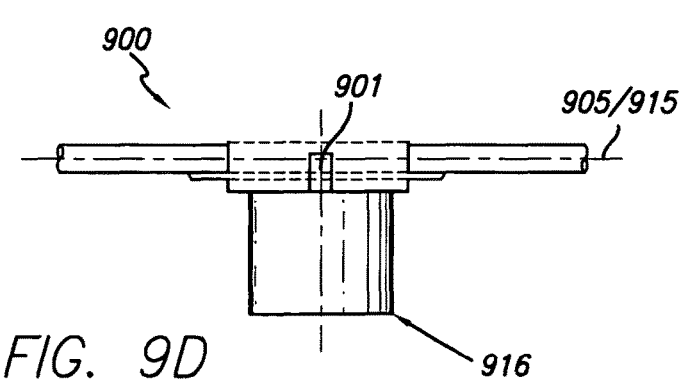

FIG. 8 shows a control device 800 that clamps the tubing from a relative outside position. Rotating element 801 includes a support member 802 that sits below the two tubes 805 and 815, and are pinched by vertical elements 803 and 804. FIG. 8B shows the control device 800 in a non contact orientation. FIG. 8C is a side view of control device 800 showing rotating support member or stepper motor 806. Again, vertical elements 803 and 804 may be formed of any material sufficient to deform the tubing. A rigid support wall (not shown) may be provided between tubes 805 and 815 to provide support when pinching.

FIG. 9 illustrates another aspect of a control device 900 for providing modulated irrigation and aspiration. Control device 900 provides for dual pinching orientations which may facilitate aspiration and irrigation in certain instances. FIG. 9A shows dual pinch member 901 pinching two tubes 905 and 915 and having center point 902 and rigid elements 903 and 904. Support may be provided such as in the form of support members 906 and 907. FIG. 9B shows the control device in the relaxed or non-pinching state. FIG. 9C illustrates the alternate pinching orientation. FIG. 9D illustrates a side view of control device 900 including rotating support member or stepper motor 916.

Figure 10A:
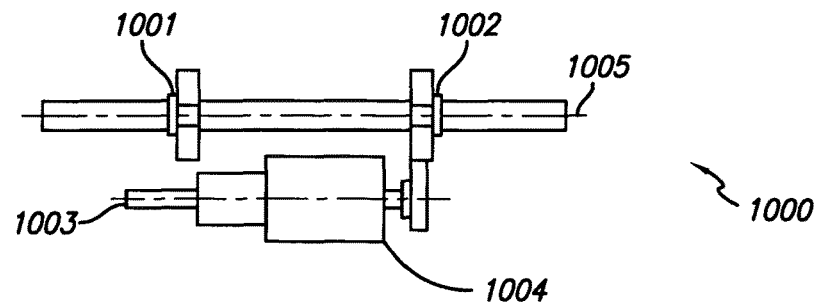
FIG. 10 illustrates a stretching type fluid control design in accordance with another aspect of the present design.
Figure 10B:
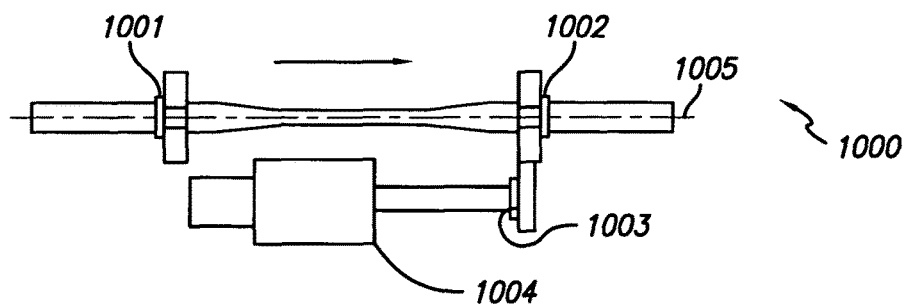

FIG. 10 illustrates a tube stretching design for a control device 1000 using a fixed piece 1001 and a movable piece 1002. The movable piece is affixed or fixedly mounted to a slidable element or plunger 1003 that slides along a sleeve 1004 to stretch the tubing 1005. FIG. 10A illustrates an unstretched aspect of the design, while FIG. 10B shows a fully extended version of the design. As may be appreciated, stretching in this manner can limit flow to a certain extent, but some minute fluid flow may continue even in the state presented in FIG. 10B. Deformation of tubing in this manner can cause wear on the tubing, so a high elasticity tubing may be employed to provide sufficient strength and extension/contraction characteristics.

Figure 11A:
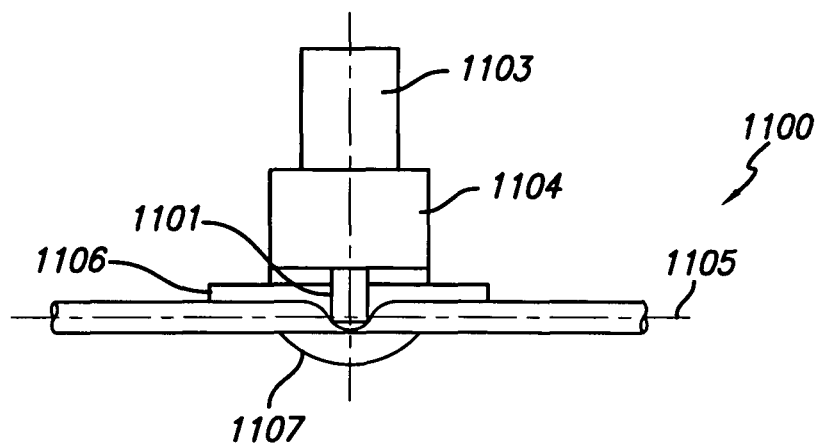
FIG. 11 is a hammer type fluid control design in accordance with another aspect of the present design.
Figure 11B:
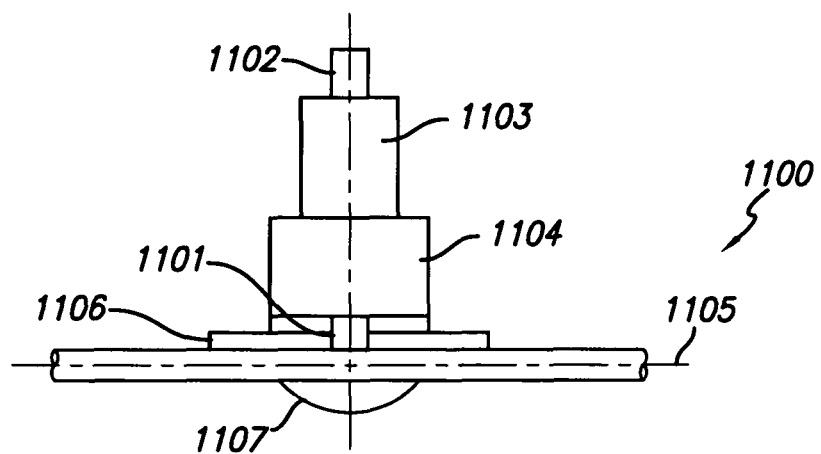
Figure 12A:
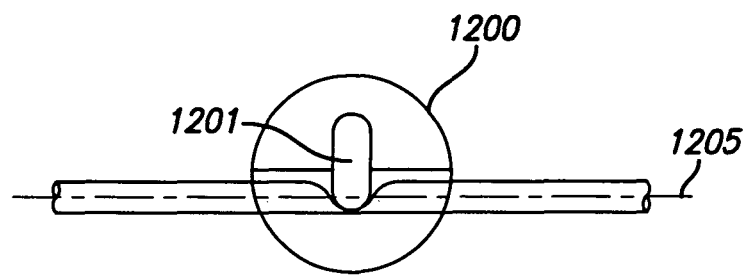
FIG. 12 presents a single hammer conceptual illustration in accordance with another fluid control aspect of the present design.
Figure 12B:
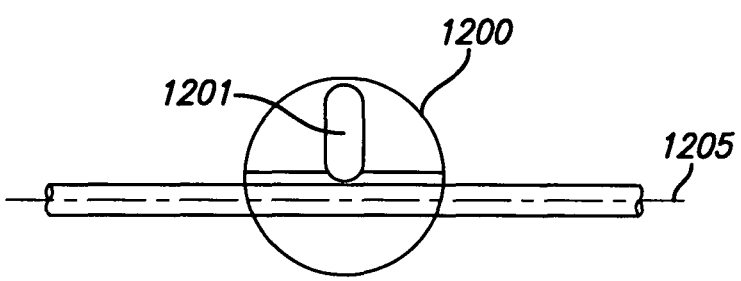

An alternate implementation is illustrated in FIG. 11, representing a hammer type design. From FIG. 11, a single hammer 1101 may be used to deform tube 1105. FIG. 11A shows the hammer type control device 1100 deforming the tube 1105, while FIG. 11B shows the hammer type control device 1100 in a nonextended state. The hammer 1101 may be actuated by movable element 1102 which slides through small sleeve 1103 and larger sleeve 1104. The movable element 1102 forces the hammer 1101 through a plate 1106 to deform tube 1105. A support member 1107 may be provided to establish resistance for the tube 1105. FIG. 12A shows a slidable single element 1201 deforming a tube 1205 while FIG. 12B shows such the slidable single element 1201 in a non-deforming state.

Figure 13A:
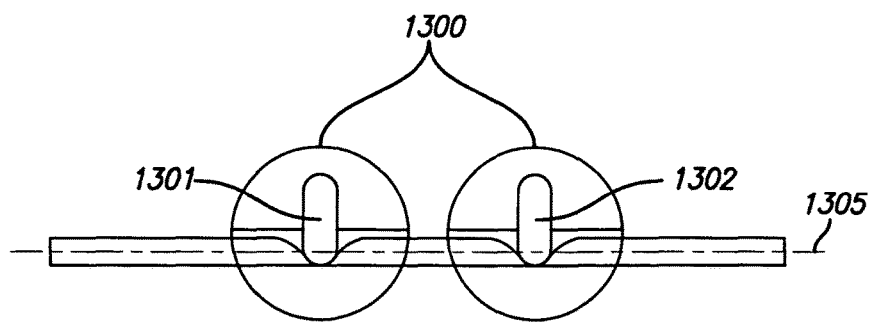
FIG. 13 shows a dual hammer conceptual illustration in accordance with another fluid control aspect of the present design.
Figure 13B:
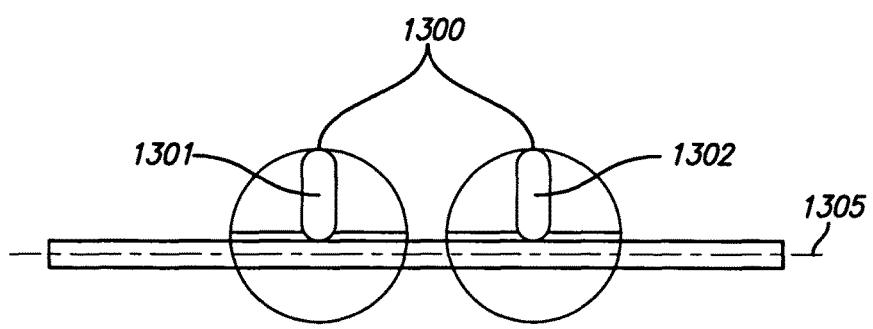
Figure 14A:
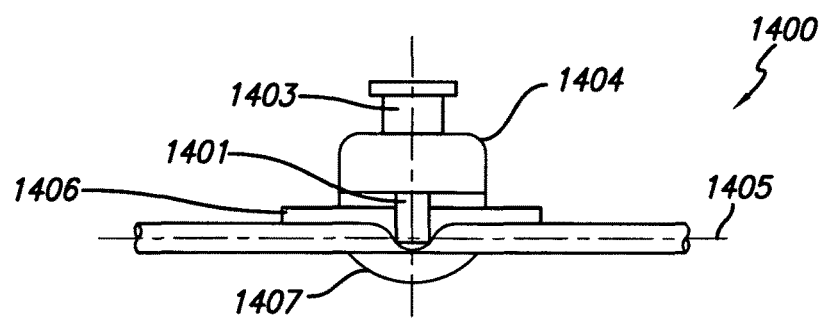
FIG. 14 illustrates an alternate hammer design in accordance with another fluid control aspect of the present design.
Figure 14B:
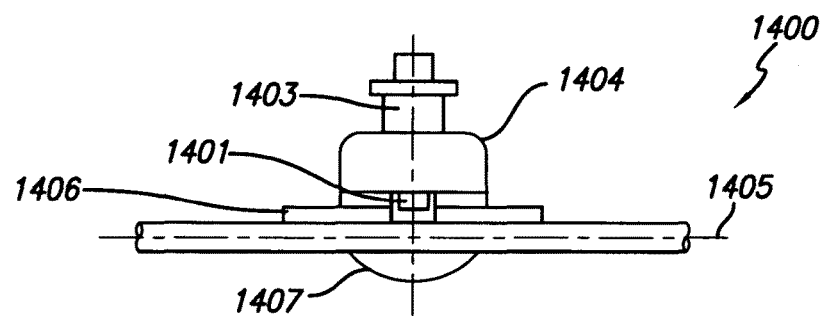

FIG. 13 shows a dual hammer approach similar to the device of FIG. 12, with a dual hammer control device 1300 comprising first hammer 1301 and second hammer 1302 used to deform tubing 1305. Ability to bind the tubing at two points can provide quicker response and more accurate inhibition of fluid flow and may be preferable in certain applications. FIG. 14 shows an alternate construct of a hammer design similar to that presented in FIG. 11. Again, FIG. 14A shows the hammer type control device 1400 deforming the tube 1405, while FIG. 14B shows the hammer type control device 1400 in a nonextended state. The hammer 1401 may be actuated by movable element 1402 which slides through small sleeve 1403 and larger rounded sleeve 1404. The movable element 1402 again forces the hammer 1403 through a plate 1406 to deform tube 1405. A support member 1407 may be provided to establish resistance for the tube 1405.

All of the foregoing control devices and any logical extensions, altered designs, or variations thereof may provide the ability to permit and restrict irrigation and/or aspiration at a very high rate. In certain applications, the foregoing designs may provide flow interruption and initiation at a periodic rate of as low as less than or approximately 2 to 100 milliseconds.

In operation, the system may use the aspiration control unit and/or irrigation control unit or device to produce a pulse pressured wave that assists in acquiring and fixing tissue on the handpiece tip. Upon initiation of ultrasonic action, instantaneous repellant forces and chatter from the ultrasonically driven handpiece tip can be overcome by a single or multiple micropressure wave transmission which tend(s) to propagate within the aspirating tubing and retract the tissue toward the handpiece tip. The micropressure wave may be used prior to inception or formation of the cavitation field and may continue in concert with the modulated ultrasonic action.

Alternately, the system may employ the pulsed pressure wave generated by one of the aforementioned control devices to disrupt the cavitation cloud. A series of high frequency pulses are employed to disrupt the cavitation cloud. The system uses a series of high frequency fluid pulses to encourage collapse of the field and improve reacquisition of tissue on the distal end of the handpiece tip. Pulses may vary in frequency and duration, but as noted, the fluid pulses may be in the range of approximately 2 to 100 milliseconds long.

The system may also use micropressure waves to dislodge or realign fragmented particulates within the aspiration lumen. The aspiration lumen is the lumen or narrow passageway used in the handpiece to collect fluid from the affected area or region. The system generates vibratory pressure waves terminating at the tip, thereby creating a lubricious surface and reducing the effective surface tension within the tubing and particularly the small piece that is with the eye. Alternately, the system may achieve high vacuum levels by controlling flow and resultant surge created by a given high vacuum level. The source can be vacuum based and may regulate flow by the pressure pulse frequency and duty cycle.

As may be appreciated by those skilled in the art, various fluid pulse timing schemes and associations with ultrasonic power delivery timing sequences may be employed. The goal of varying the time and power is to attain transient cavitation in a relatively rapid manner and enable acquisition of material in the environment presented without generating significant heat. Timing of the fluid pulses may be coordinated with the ultrasonic power delivery timing or may be different depending on circumstances. For example, ultrasonic power delivery may include a two step modulated pulse including providing a pulse of energy at level X for M ms, followed by a pause or de minimis power application for N ms. Fluid may be supplied at the same M and N timing scheme, or at a fluid pulse on for 2*M ms and off for N ms, or on for P ms and off for Q ms. Additionally, multiple levels of power may be applied, such as one period at level X, one period at level Y, and one period at level Z, followed by a pause. The duty cycle, period, power level, and fluid level for the system may vary depending on circumstances.

While various timing sequences may be employed, it is generally understood that fluid irrigation pulses have duration generally less than 100 ms when operating in accordance with the present design. In certain circumstances and in certain environments, this number may be in the range of 25, 20, 8, or even 2 ms. In transmitting certain pulse schemes, such as those required to facilitate transient cavitation, a relatively high amplitude pulse may be delivered for in the range of generally less than approximately 25 ms, and in certain scenarios and environments, less than 10, 5, or even 2 ms. Aspiration by means of application of negative pressure differential pulses may be for similar periods, and generally operates in the range of less than 100 ms.

Figure 15:
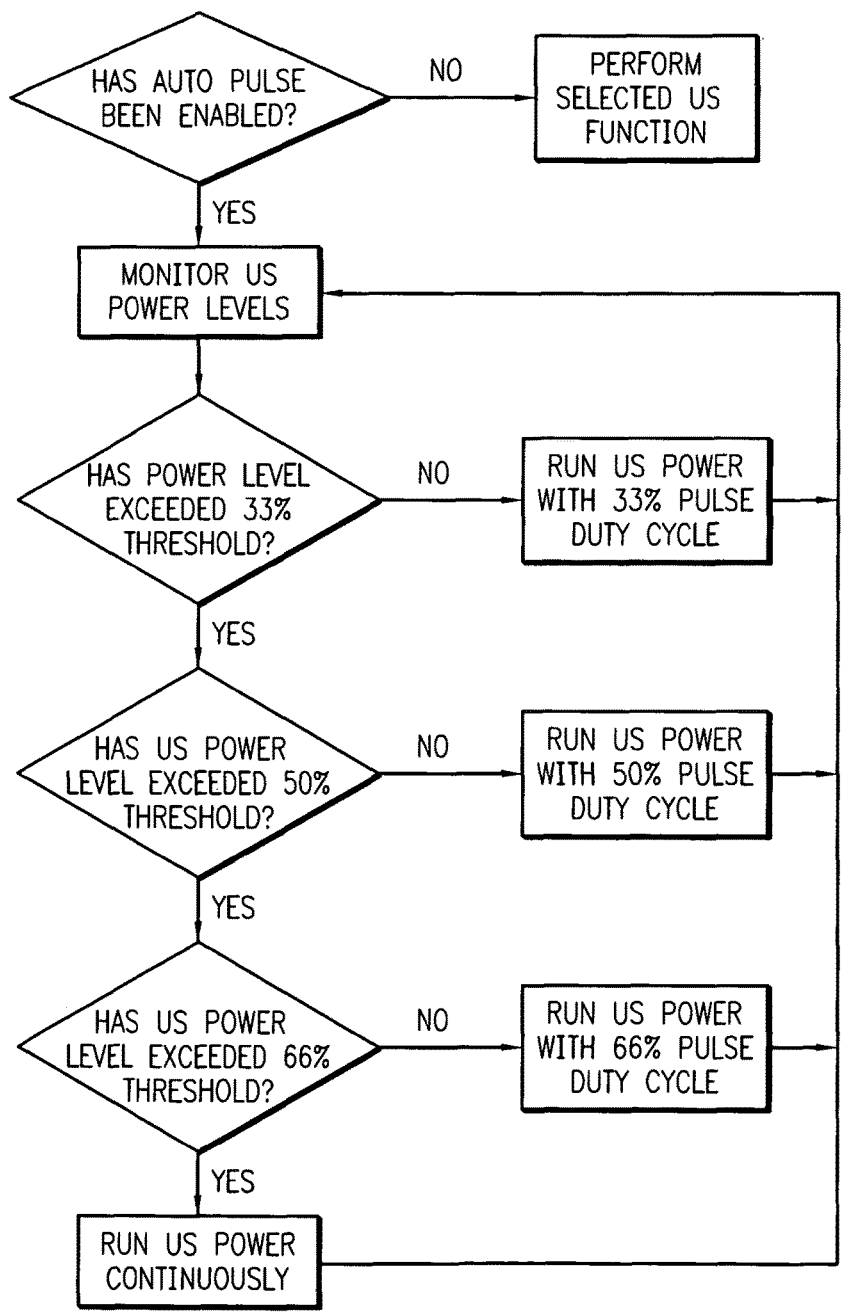
FIG. 15 is a flow chart illustrating the operation of a variable duty cycle pulse function of the ultrasound energy delivery aspect of the phacoemulsification system.

The present phacoemulsification system is set up to address occlusions using both modulated energy delivery and modulated energy delivery in combination with altered fluid delivery. With reference to FIG. 15, there is shown a flow diagram depicting basic control of the ultrasonic power source 16 to produce varying pulse duty cycles as a function of selected power levels. Each power pulse may have a duration of less than 20 milliseconds. As shown in FIG. 5, and by way of illustration only, a 33% pulse duty cycle is run until the power level exceeds a preset threshold; in this case, 33%. At that point, the pulse duty cycle is increased to 50% until the ultrasonic power level exceeds a 50% threshold, at which point the pulse duty cycle is increased to 66%. When the ultrasonic power level exceeds 66% threshold, the power source is run continuously, i.e., a 100% duty cycle. Although the percentages of 33, 50 and 66 have been illustrated in FIG. 15, it should be understood that other percentage levels can be selected as well as various duty cycles to define different duty cycle shift points. The pulse duration in this arrangement may be less than 20 milliseconds. This control along with the tracking mechanism herein described enables bursts of energy less than 20 milliseconds in duration. With reference to FIG. 15, if the handpiece aspiration line 38 is occluded, the vacuum level sensed by the vacuum sensor 24 will increase. Irrigation may be supplied by one or two or more sources. The computer 18 has operator-settable limits for controlling which of the irrigation fluid supplies 32, 33 will be connected to the handpiece 30. While two irrigation fluid sources, or containers 32, 33 are shown, any number of containers may be utilized.

Figure 16:
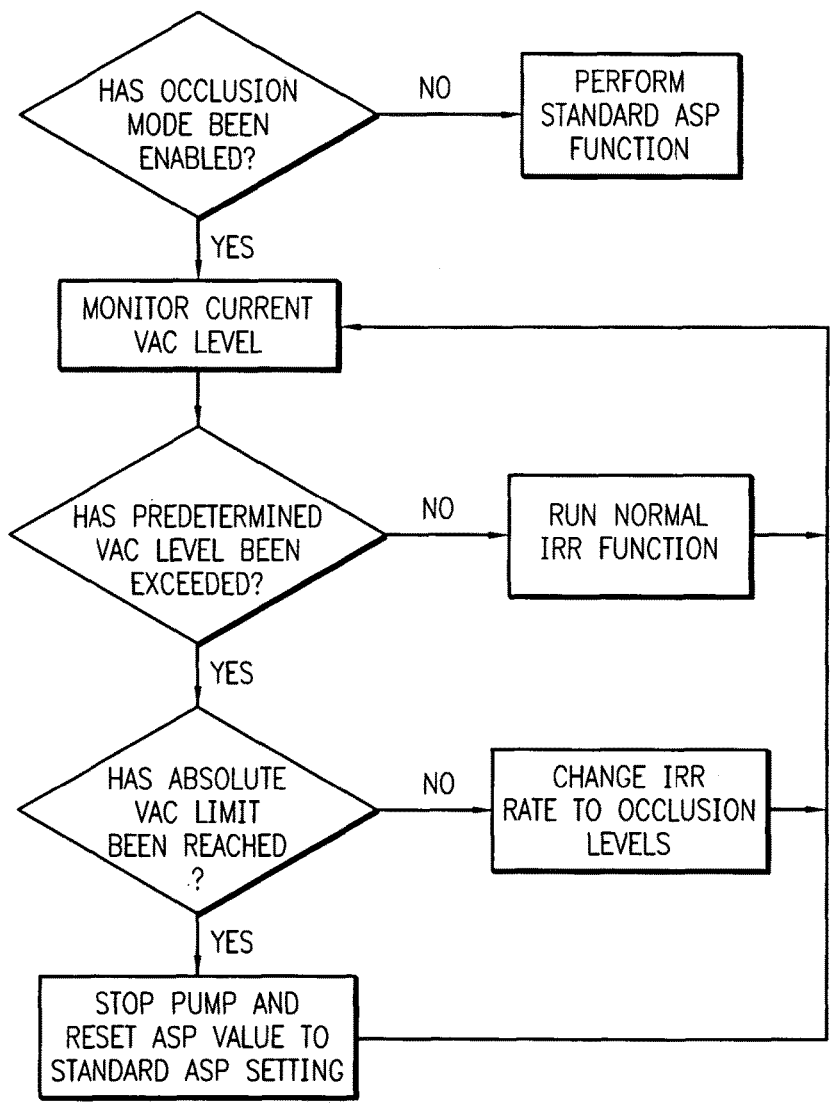
FIG. 16 is a flow chart illustrating the operation of the occluded-unoccluded mode of the ultrasound energy delivery aspect of the phacoemulsification system with variable irrigation rates, including pulsed fluid delivery.

As shown in FIG. 16, when the vacuum level by the vacuum sensor 24 reaches a predetermined level, as a result of occlusion of the aspiration handpiece line 38, the computer further controls the valve 38 causing the valve to control fluid communication between each of the containers 34, 35 and the handpiece/needle 30.

Depending upon the characteristics of the material occluding the handpiece/needle 30, as herein described and based on the needs and techniques of the physician, the pressure and fluid pulse period and pulse duty cycle of irrigation fluid provided to the handpiece may be increased or decreased. As occluded material is cleared, the vacuum sensor 24 may register a drop in the vacuum level causing the valve 38 to switch to a container 34, 35, providing pressure at an unoccluded level.

In addition to changing phacoemulsification handpiece/needle 30 parameters as a function of encountered vacuum level, the occluded or unoccluded state of the handpiece can be determined and addressed based on a change in load sensed by a handpiece/needle by way of a change in phase shift or shape of the phase curve. A plot of phase angle as a function of frequency is shown in FIG. 17 for various handpiece 30 loading, a no load (max phase), light load, medium load and heavy load.

Figure 17:
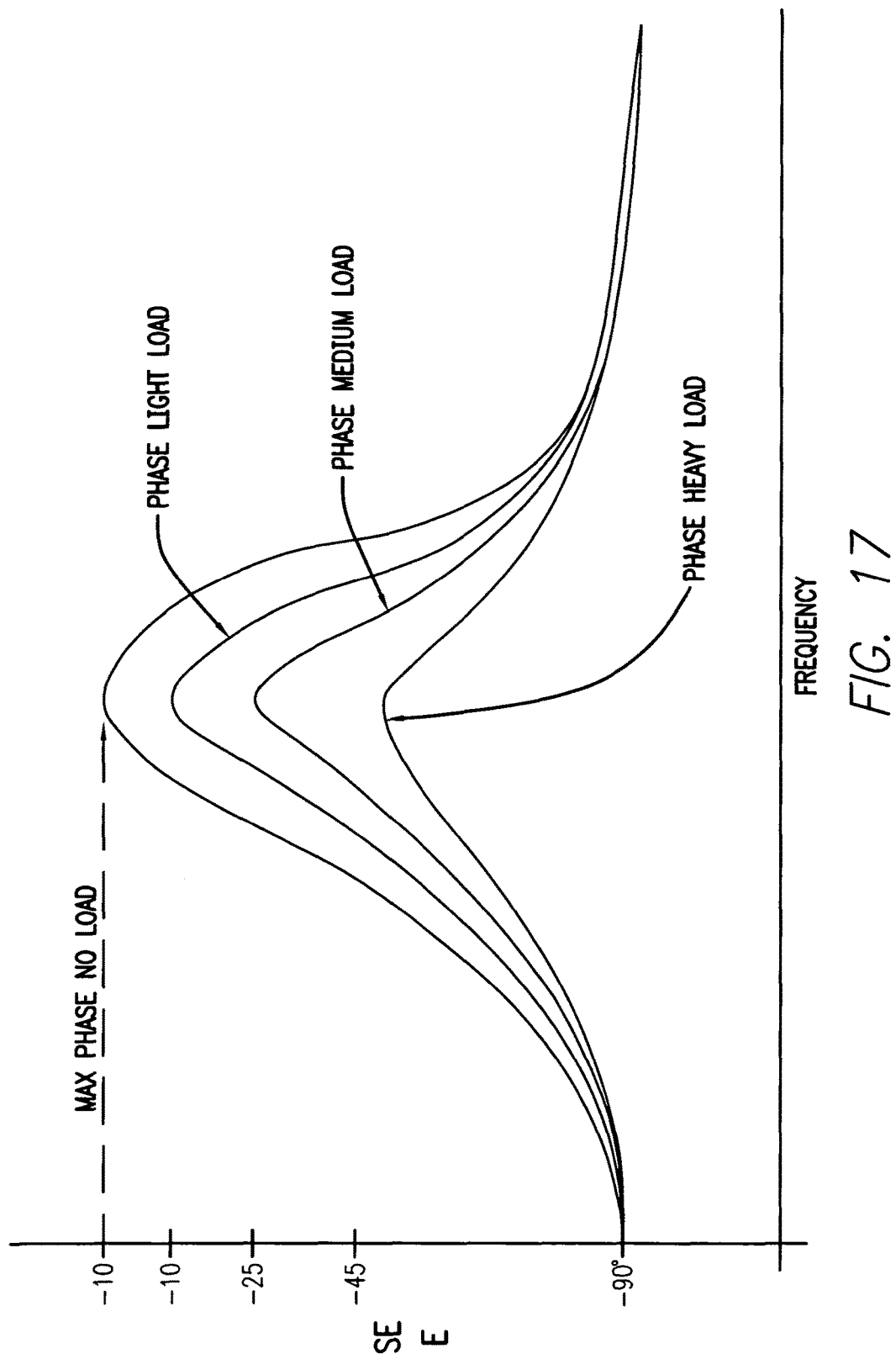
FIG. 17 is a plot of the phase relationship of ultrasound energy delivery as a function of frequency for various handpiece/needle loading.
Figure 18:
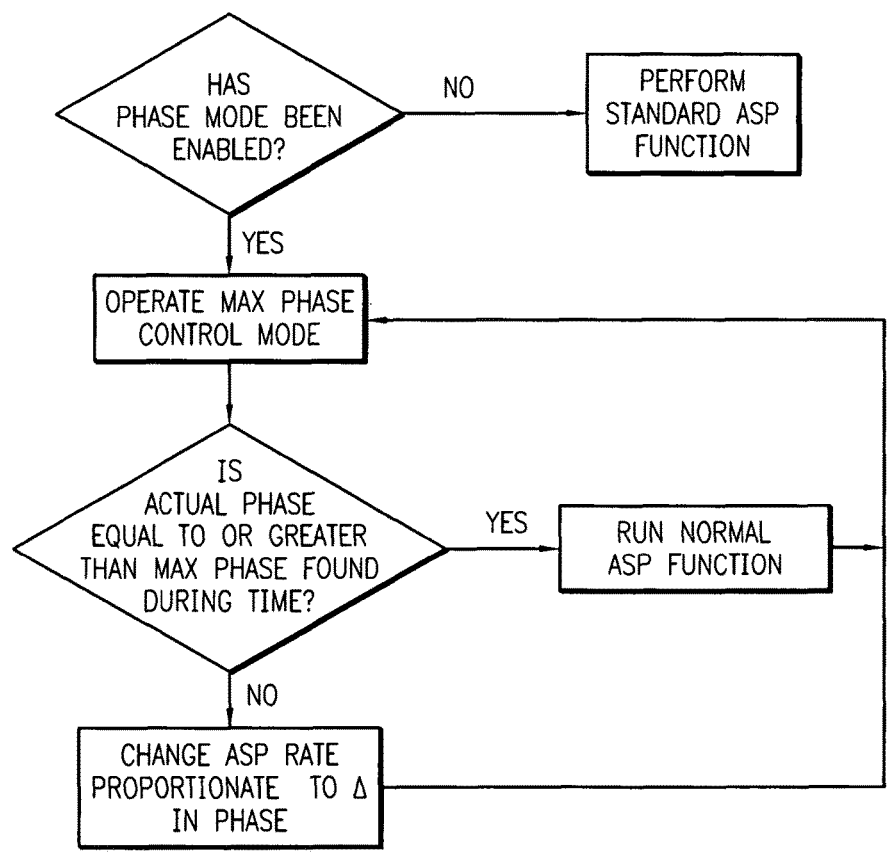
FIG. 18 is a function block diagram of phase control ultrasound energy delivery in a phacoemulsification system utilizing phase angles to control handpiece/needle parameters with max phase mode operation.
Figure 19:
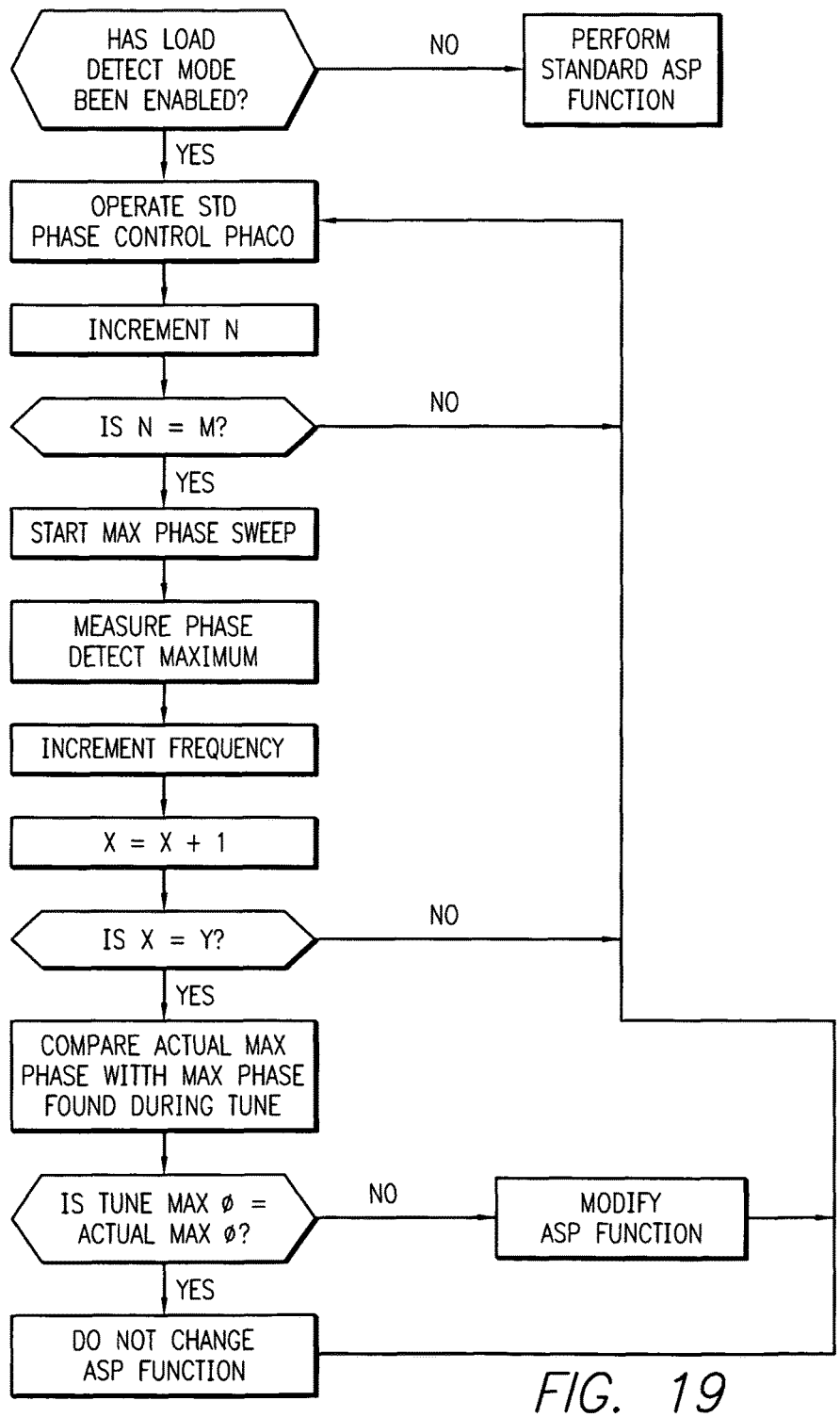
FIG. 19 is a function block control diagram of a phase control ultrasound energy delivery in a phacoemulsification system utilizing phase angles to control handpiece/needle parameters with a load detect method.

With reference to FIG. 18, representing max phase mode operation, the actual phase is determined and compared to the max phase. If the actual phase is equal to, or greater than, the max phase, normal aspiration function is performed. If the actual phase is less than the max phase, the aspiration rate is changed, with the change being proportionate to the change in phase. FIG. 19 represents operation at less than max load in which load (see FIG. 17) detection is incorporated into the operation.

As represented in FIG. 18, showing max phase mode operation, if the handpiece aspiration line 40 is occluded, the phase sensed by phase detector sensor 28 will decrease (see FIG. 17). The computer 18 provides operator-settable limits for aspiration pulse rates, vacuum levels and ultrasonic power levels. As illustrated in FIG. 18, when the phase sensed by phase detector 28 reaches a predetermined level as a result of occlusion of the handpiece aspiration line 40, computer 18 instructs pump speed controller 20 to change the speed of the peristaltic pump 14 which, in turn, changes the aspiration rate and/or aspiration pulse rate.

Depending upon the characteristics of the material occluding handpiece/needle 30, the speed of the peristaltic pump 14 can either be increased or decreased. When the occluding material is broken up, the phase detector 28 registers an increase in phase angle, causing computer 18 to change the speed of peristaltic pump 14 to an unoccluded operating speed.

In addition to changing the phacoemulsification parameter of aspiration rate or aspiration pulse rate by varying the speed of the peristaltic pump 14, the power level and/or duty cycle of the ultrasonic power source 16 can be varied as a function of the occluded or unoccluded condition of handpiece 30 as hereinabove described.

From the foregoing, depending on output conditions, cavitation may be generated in different circumstances by the ultrasonic device, and cavitation inducing energy may be employed with pulsed fluid application. This cavitation and pulsed fluid application may be employed in varying environments in addition to those disclosed herein, including but not limited to a diagnostic environment and a chemical processing environment. The cavitation and pulsed fluid application may also be employed in medical treatments or to enhance medical treatments. Enhancement of medical treatments may include, for example, assisting or accelerating the medical treatment. With respect to chemical processing, applying energy and fluid in the manner described can have a tendency to minimize heat resulting from ultrasound energy transmission, and can tend to minimize input energy required to effectuate a given chemical result.

Transient cavitation tends to require certain specific conditions to occur effectively in the phaco environment, including but not limited to the availability of properly sized initial bubbles and/or dissolved gas in the fluid. When bubbles of the proper size and/or dissolved gas are not available, either because of low flow or in the presence of a high output level in a continuous power application mode, transient cavitation tends to transition to stable cavitation. Pulsing energy and fluid as opposed to constant energy and fluid can provide certain advantages, such as enabling the fluid to resupply properly sized bubbles to facilitate transient cavitation, consuming and delivering less total power with less likelihood of causing thermal damage to tissue.

Figure 20:
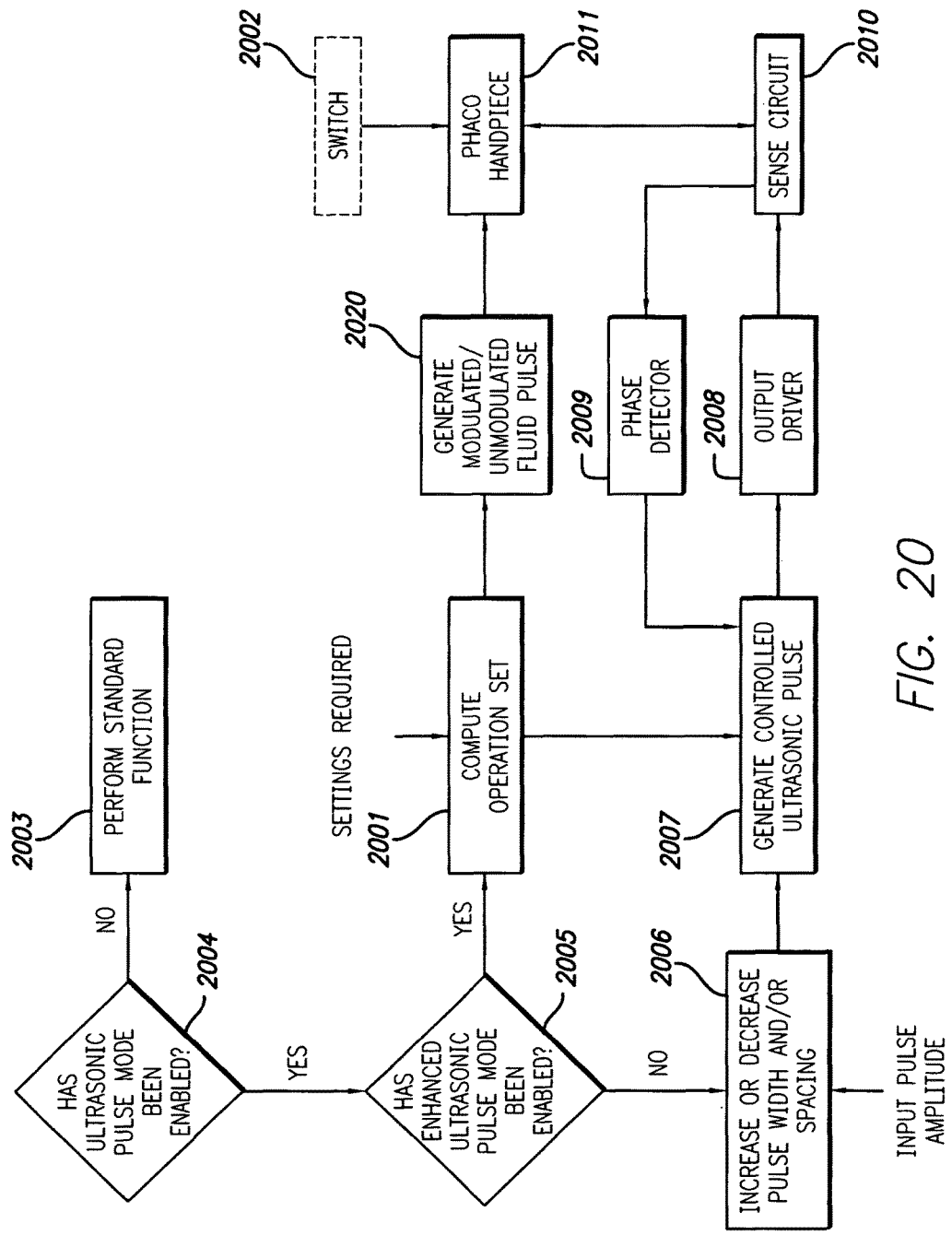
FIG. 20 presents a conceptual block diagram of computation and delivery of an enhanced ultrasonic energy waveform.
Figure 21:
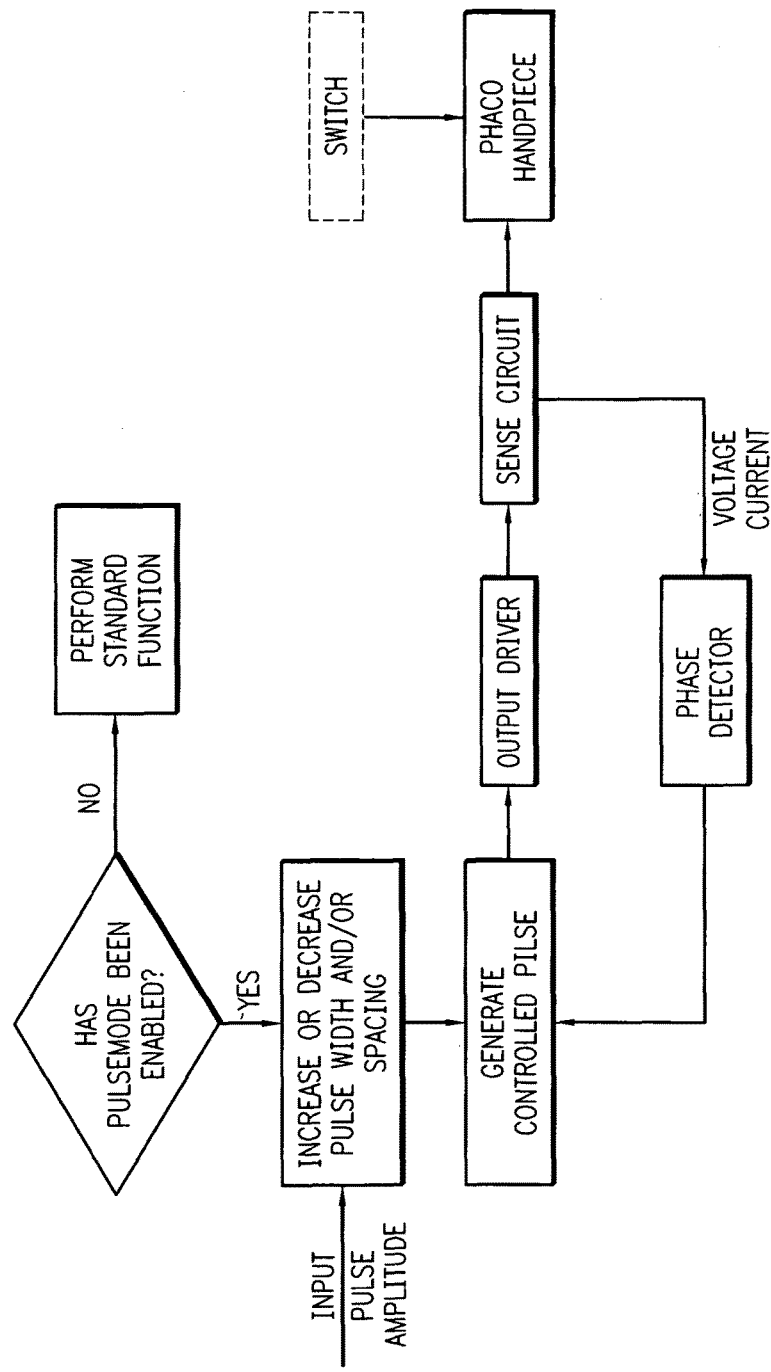
FIG. 21 is a function block control diagram of a pulse control phacoemulsification system with normal ultrasonic energy waveforms.

The pulsing of energy and fluid described herein may be performed in software, hardware, firmware, or any combination thereof, or using any device or apparatus known to those skilled in the art when programmed according to the present discussion. A sample block diagram of the operation of the pulsed energy and pulsed fluid aspect of the system as may be implemented in software is presented in FIG. 20. From FIG. 20, after evaluating whether pulse mode has been enabled, the system evaluates whether enhanced pulse mode has been enabled. If not, the system proceeds according to FIG. 21.

If enhanced pulse mode has been enabled, the Settings Required are received. Settings Required may include, but are not limited to, overall cycle time, a desired procedure or function to be performed (sculpting, chopping, etc.), desire to provide bursts or long continuous periods of power application, desired transient cavitation energy application amplitude, desired transient cavitation energy application period, desired lower amplitude energy level, desired lower amplitude energy duration, pause between transient application energy bursts, fluid pulse duration, fluid pulse duty cycle, fluid amplitude, fluid pause duration, and/or other pertinent information. Certain lookup tables may be provided in determining Settings Required, including but not limited to tables associating popular settings with the specific performance parameters for the desired setting. For example, if the desired function is "chop," the system may translate the desired "chop" function selection into a standardized or predetermined set of performance parameters, such as a 150 millisecond ultrasonic energy "burst on" period, followed by an 350 ms "long off period," and an associated 100 millisecond fluid pulse on period followed by a 200 millisecond fluid pulse off period. The system takes the Settings Required and translates them into an Operation Set, or operation timing set, the Operation Set indicating the desired operation of the phacoemulsification handpiece tip when performing ultrasonic energy or power delivery as well as fluid application.

Input 2002 represents an optional input device, such as a foot pedal, electronic or software switch, switch available on the phacoemulsification handpiece, or other input device known to those skilled in the art, that allows the surgeon/operator to engage and enable ultrasonic power and fluid to be applied according to the Operation Set. For example, a foot pedal may be supplied that issues an on/off command, such that when depressed power and fluid are to be applied according to the Operation Set, while when not depressed power is not supplied to the phacoemulsification handpiece tip and fluid is applied at a predetermined constant flow rate.

Different input devices may enable different modes of operation. For example, a multiple position switch may be provided that allows for application of ultrasonic power and fluid according to one Operation Set, while moving the switch to another position allows for application of ultrasonic power and fluid according to a different Operation Set. Alternately, one position of the switch may allow for power application and fluid at one level according to one Operation Set, while another position of the switch may enable a higher ultrasonic power level and different fluid level having the same or a different operational timing set. Operation Set as used herein refers to the timing of ultrasonic energy pulses, energy applications, fluid applications, and/or on/off periods for the application of power and fluid as described herein. Switching may also be nonlinear, such as one detent or setting for the switch providing only pulsed irrigation to the handpiece 30, a second detent or setting providing a pump on plus pulsed irrigation, and a third detent or setting providing irrigation and aspiration wherein ultrasound is introduced and may be increased by applying further engagement of the switch or foot pedal. In this instance, a foot pedal depressed to the third position or detent will enable the operator or surgeon to apply energy according to a base operational timing set and amplitude, such as a first operational timing set with a first transient cavitation inducing amplitude, while further depression of the foot pedal would allow application of a second operational timing set and/or a second amplitude. If increased energy or fluid amplitude is desired, depressing the foot pedal past the third detent may linearly change the amplitude from a value of 0% of available ultrasonic power or tip stroke length as well as fluid pulse level to a value of 100% of ultrasonic power/tip stroke length and fluid pulse level, or some other value between 0% and 100%.

As may be appreciated, virtually any Operation Set and operation timing set may be employed while within the course and scope of this invention. In particular, the system enables operation in multiple configurations or operational timing sets, each typically accessible to the user via the computer. For example, the user may perform a chop operation using one operational timing set, a sculpt operation using another operational timing set, and when encountering particular special conditions employing yet another operational timing set. These configurations may operate dynamically, or "on the fly."

The system typically has a frame rate, which may be any period of time less than the smallest allowable power on/power off period or fluid on/fluid off period for the device. A counter counts the number of pulses, and if the Operation Set dictates that ultrasonic power or fluid is to be delivered at a certain frame number, an indication in the form of an electronic signal is delivered to the handpiece tip at that frame time. Other implementations beyond that shown in FIG. 20 may be employed while still within the scope of the present invention.

It will be appreciated to those of skill in the art that the present design may be applied to other systems that perform tissue extraction, such as other surgical procedures used to remove hard nodules, and is not restricted to ocular or phacoemulsification procedures. In particular, it will be appreciated that any type of hard tissue removal, sculpting, or reshaping may be addressed by the application of pulsed fluid in the manner described herein.

Although there has been hereinabove described a method and apparatus for providing modulated fluid to a phacoemulsification handpiece utilizing a fluid control device, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. An apparatus comprising:
   a handpiece having a needle and electrical components configured to ultrasonically vibrate said needle;
   a power source configured to provide pulsed electrical power to the handpiece electrical components;
   a computing device configured to enable an operator to select an amplitude of the electrical pulses; and
   an irrigation control unit configured to provide fluid during a surgical procedure conducted in a surgical environment by deforming tubing providing fluid during a surgical procedure, said irrigation control unit configured to provide fluid in a controlled nonrandom manner during at least one modulated fluid burst period, said modulated fluid burst period comprising a fluid pulse within the surgical environment, followed by a de minimis fluid pulse;
   wherein the apparatus is configured to induce transient cavitation the surgical environment by controlling the handpiece to produce ultrasonic energy pulses at the amplitude for a duration of less than 20 milliseconds while the irrigation control unit is configured to simultaneously provide at least one pressure pulse having a duration of less than 100 milliseconds.

2. The apparatus of claim 1, said irrigation control unit comprising a fluid control device providing an ability to modulate fluid pulses having duration less than 100 milliseconds.

3. The apparatus of claim 1, wherein said handpiece, power source, and computing device are configured to provide ultrasonic power during at least one modulated energy delivery period.

4. The apparatus of claim 3, wherein said modulated energy delivery period operates in conjunction with the modulated fluid burst period to enhance effects of a surgical procedure.

5. The apparatus of claim 4, wherein enhancing effects of the surgical procedure comprises improving acquisition and removal of tissue during the surgical procedure.

6. The apparatus of claim 4, wherein enhancing effects of the surgical procedure comprises enhancing effects from cavitation forces encountered during the surgical procedure.

7. The apparatus of claim 1, wherein said irrigation control unit is further configured to provide a subsequent nonzero amplitude fluid pulse.

8. The apparatus of claim 7, wherein amplitude of said subsequent nonzero amplitude fluid pulse materially differs from amplitude of said fluid pulse.

9. The apparatus of claim 7, wherein amplitude of said subsequent nonzero amplitude pulse is substantially identical to amplitude of said fluid pulse.

10. The apparatus of claim 1, wherein the fluid pulse produced by the irrigation control unit has a duration of at most approximately 25 milliseconds.

11. The apparatus of claim 1, wherein the fluid pulse produced by the irrigation control unit has a duration of at most approximately 8 milliseconds.

12. The apparatus of claim 1, wherein the handpiece and the computing device are configured to engage operation at a first desired time when energy application is desired and disengage operation at a second desired time when energy application is not desired.

13. The apparatus of claim 12, wherein the handpiece and the computing device are configured to engage modulated irrigation at the first desired time and disengaged at the second desired time when modulated irrigation is not desired.

14. The apparatus of claim 12, wherein said handpiece comprises a switch.

15. An apparatus comprising:
    a handpiece having a needle and electrical components configured to ultrasonically vibrate said needle;
    a power source configured to provide pulsed electrical power to the handpiece electrical means;
    a computing device configured to enable an operator to select an amplitude of the electrical pulses; and
    an irrigation control unit configured to provide fluid from the handpiece, said irrigation control unit configured to control fluid provided in a controlled nonrandom manner by applying fluid for a fluid pulse period followed by applying de minimis fluid during a fluid pause period by deforming tubing providing fluid during a surgical procedure;
    wherein the apparatus is configured to induce transient cavitation the surgical environment by controlling the handpiece to produce ultrasonic energy pulses at the amplitude for a duration of less than 20 milliseconds while the irrigation control unit is configured to simultaneously provide at least one pressure pulse having a duration of less than 100 milliseconds.

16. The apparatus of claim 15, wherein said irrigation control unit comprises a fluid control device providing an ability to modulate fluid pulses having duration less than 100 milliseconds.

17. The apparatus of claim 15, wherein said power source and said computing device controls power provided by the handpiece by providing ultrasonic power during at least one modulated energy delivery period.

18. The apparatus of claim 17, wherein said power source operates in timing relationship with the irrigation control unit to enhance effects of a surgical procedure.

19. The apparatus of claim 18, wherein enhancing effects of the surgical procedure comprises improving acquisition and removal of tissue during the surgical procedure.

20. The apparatus of claim 18, wherein enhancing effects of the surgical procedure comprises enhancing effects from cavitation forces encountered by the apparatus during the surgical procedure.

21. The apparatus of claim 15, wherein the lower energy period comprises applying fluid during the fluid pulse period at an amplitude selected using the computing device.

22. The apparatus of claim 15, wherein the apparatus provides an ability to operate within an ocular environment, and further wherein power supplied by the handpiece induces transient cavitation within the ocular environment thereby enabling cutting of ocular tissue.

23. The apparatus of claim 15, wherein said irrigation control unit controls fluid by further applying fluid for an additional nonzero fluid pulse period.

24. The apparatus of claim 15, wherein the handpiece and the computing device are configured to engage operation at a first desired time when ultrasonic energy application is desired and disengage at a second desired time when ultrasonic energy application is not desired.

25. The apparatus of claim 24, wherein said handpiece and computing device further control fluid application via the irrigation control unit.

26. The apparatus of claim 24, wherein said handpiece comprises a switch.

27. A surgical apparatus, comprising:
an ultrasonic power source configured to provide pulsed ultrasonic power to a handpiece; and
an irrigation control unit configured to apply modulated fluid pulses in a controlled nonrandom manner during a plurality of short burst periods by deforming tubing providing fluid during a surgical procedure, said short burst periods comprising a fluid burst period followed a predetermined time thereafter by a de minimis fluid delivery period;
wherein the ultrasonic power source is configured to induce transient cavitation by providing pulsed ultrasonic power at a selected amplitude for a duration of less than 20 milliseconds concurrently with the irrigation control unit simultaneously providing aspiration by application of at least one pressure pulse having duration of less than 100 milliseconds.

28. The apparatus of claim 27, said irrigation control unit comprises tubing and fluid maintenance containers, wherein said fluid maintenance containers provide fluid to the tubing, and wherein said tubing carries fluid to the irrigation control unit.

29. The apparatus of claim 27, wherein the ultrasonic power source is configured to provide ultrasonic power during at least one modulated energy delivery period.

30. The apparatus of claim 29, wherein said ultrasonic power source operates in timing relationship with the irrigation control unit to enhance effects of a surgical procedure.

31. The apparatus of claim 30, wherein enhancing effects of the surgical procedure comprises improving acquisition and removal of tissue during the surgical procedure.

32. The apparatus of claim 30, wherein enhancing effects of the surgical procedure comprises enhancing effects from cavitation forces encountered by the apparatus during the surgical procedure.

33. The apparatus of claim 29, wherein said ultrasonic power source operates using a different timing sequence than a timing sequence used by the irrigation control unit, thereby enhancing effects of a surgical procedure.

34. The apparatus of claim 29, wherein said ultrasonic power source delivers ultrasonic energy in a plurality of short burst periods interspersed by multiple de minimis power application periods.

* * * * *